United States Patent
Vogt et al.

(10) Patent No.: US 12,144,971 B2
(45) Date of Patent: Nov. 19, 2024

(54) DEVICE FOR TEMPORARILY, LOCALLY APPLYING FLUIDS

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 606 days.

(21) Appl. No.: 17/025,653

(22) Filed: Sep. 18, 2020

(65) Prior Publication Data
US 2021/0077739 A1    Mar. 18, 2021

(30) Foreign Application Priority Data

Sep. 18, 2019 (EP) ...................................... 19198038
Jan. 27, 2020 (EP) ...................................... 20153853

(51) Int. Cl.
*A61M 5/315* (2006.01)
*A61M 5/31* (2006.01)

(52) U.S. Cl.
CPC .... *A61M 5/31511* (2013.01); *A61M 5/31525* (2013.01); *A61M 5/31576* (2013.01);
(Continued)

(58) Field of Classification Search
CPC ............ A61M 25/0012; A61M 25/007; A61M 25/0015; A61M 25/0014; A61M 25/0021;
(Continued)

(56) References Cited

U.S. PATENT DOCUMENTS 3,583,387 A * 6/1971 Garner .................. A61M 25/02
                                                              600/561
3,888,249 A   6/1975 Spencer
(Continued)

FOREIGN PATENT DOCUMENTS

DE    28 43 963    4/1980
DE    32 03 957    8/1983
(Continued)

OTHER PUBLICATIONS

Kühn et al. (K.-D. Kühn, N. Renz, A. Trampuz: Lokale Antibiotika-Therapie (Local antibiotic therapy). Der Unfallchirurg. 120 (2017) 561-572.
(Continued)

*Primary Examiner* — Robert J Utama
*Assistant Examiner* — Justin L Zamory
(74) *Attorney, Agent, or Firm* — Dicke, Billig & Czaja, PLLC

(57) ABSTRACT

One aspect relates to a device for locally applying a medical fluid, including a flexibly deformable tube including a tube wall. The tube includes a plurality of openings in the tube wall, the plurality of openings connecting an inner line of the tube to the surroundings of the tube, and the tube being closed at a distal tube. A proximal tube end of the tube is liquid-permeably connectable to a container for the medical fluid such that the medical fluid from the container can be pushed through the proximal tube end of the tube into the inner line of the tube and can be pushed out through the plurality of openings into the surroundings of the tube. The device includes an outer sleeve for closing a subset of the plurality of openings, the outer sleeve being axially movably arranged around the tube, and being shorter than the tube such that the distal openings that are not part of the closed subset of the plurality of openings are exposed.

22 Claims, 18 Drawing Sheets

(52) U.S. Cl.
CPC . *A61M 2005/3128* (2013.01); *A61M 2205/02* (2013.01); *A61M 2205/32* (2013.01); *A61M 2205/3334* (2013.01)

(58) Field of Classification Search
CPC ............ A61M 25/005; A61M 25/0068; A61M 2025/0006; A61M 2025/0175; A61M 2025/0018; A61M 39/10; A61M 5/31511; A61M 5/31525; A61M 5/31576
See application file for complete search history.

(56) References Cited

U.S. PATENT DOCUMENTS

| | | | |
|---|---|---|---|
| 4,306,563 | A | 12/1981 | Iwatschenko |
| 4,346,703 | A * | 8/1982 | Dennehey ............... A61M 5/14 |
| | | | 604/905 |
| 4,347,234 | A | 8/1982 | Wahlig et al. |
| 4,475,898 | A * | 10/1984 | Brodner .............. A61M 25/007 |
| | | | 604/9 |
| 4,963,306 | A * | 10/1990 | Weldon ............. A61M 25/0009 |
| | | | 264/209.3 |
| 4,968,306 | A | 11/1990 | Huss et al. |
| 5,380,307 | A | 1/1995 | Chee et al. |
| 5,403,291 | A * | 4/1995 | Abrahamson ....... A61M 25/007 |
| | | | 604/523 |
| 5,425,723 | A | 6/1995 | Wang |
| 5,645,528 | A | 7/1997 | Thome |
| 5,800,407 | A | 9/1998 | Eldor |
| 5,807,349 | A | 9/1998 | Person et al. |
| 6,537,194 | B1 | 3/2003 | Winkler |
| 6,719,738 | B2 * | 4/2004 | Mehier .................. A61M 5/44 |
| | | | 604/93.01 |
| 10,092,693 | B2 | 10/2018 | Hanson et al. |
| 10,406,288 | B2 | 9/2019 | Reber et al. |
| 2004/0186444 | A1 | 9/2004 | Daly et al. |
| 2006/0155250 | A1 | 7/2006 | Endo et al. |
| 2006/0229573 | A1 | 10/2006 | Lamborne |
| 2008/0300530 | A1 | 12/2008 | Massengale |
| 2009/0166913 | A1 * | 7/2009 | Guo .................. A61M 25/0012 |
| | | | 264/171.27 |
| 2011/0098653 | A1 | 4/2011 | Powers et al. |
| 2013/0274711 | A1 | 10/2013 | O'Day |
| 2014/0025039 | A1 | 1/2014 | Rajendran et al. |
| 2014/0094773 | A1 | 4/2014 | Lampropoulos et al. |
| 2015/0088051 | A1 * | 3/2015 | Ragg ................ A61B 17/12131 |
| | | | 514/723 |
| 2017/0246403 | A1 | 8/2017 | Cowe et al. |
| 2018/0369538 | A1 | 12/2018 | Lee et al. |

FOREIGN PATENT DOCUMENTS

| | | |
|---|---|---|
| DE | 33 34 595 | 4/1985 |
| DE | 34 29 038 | 2/1986 |
| EP | 1932560 | 6/2008 |
| EP | 2 656 869 | 10/2013 |
| JP | H11-506640 | 6/1999 |
| JP | 2004081883 | 3/2004 |
| JP | 2008535578 | 9/2008 |
| JP | 2014500090 | 1/2014 |
| JP | 2014087397 | 5/2014 |
| JP | 2015530153 | 10/2015 |
| JP | 2017529941 | 10/2017 |

OTHER PUBLICATIONS

K. Klemm: Gentamicin-PMMA-beads in treating bone and soft tissue infections. Zentralbl. Chir. 104(14) (1979) 934-942.

K. Klemm: Antibiotic bead chains. Clin. Orthop. 295 (1993) 63-76.

* cited by examiner

DEVICE FOR TEMPORARILY, LOCALLY APPLYING FLUIDS

CROSS-REFERENCE TO RELATED APPLICATIONS

This Utility Patent Application claims priority to European Application No. 20153853.5, filed on Jan. 27, 2020 and European Application No. 19198038.2, filed Sep. 18, 2019, both of which are incorporated herein by reference.

TECHNICAL FIELD

One aspect relates to a device for temporarily, locally applying medical fluids, in particular pharmaceutical fluids. One aspect also relates to a method for operating such a device.

BACKGROUND

The local application of pharmaceutical active ingredients, such as antibiotics, has been known for several decades and has proved effective in particular in treating or relieving infections of the bone tissue. A distinction can be made between active ingredient carriers that are non-resorbable and those that are resorbable or biodegradable. Introducing fluids into hollow spaces for the purpose of flushing and disinfection can also be useful for disinfecting and cleaning medical implants and devices having hollow spaces that would otherwise be difficult to reach.

For the medical treatment of infections in hollow spaces and cavities that are difficult to reach, such as bone cavities, resorbable and non-resorbable active ingredient carriers are known.

The bead chains known under the brand name Septopal® since 1977 are an example of non-resorbable active ingredient carriers. The bead chains consist of polymethyl methacrylate beads that contain the broad-spectrum antibiotic gentamicin sulfate, the beads being arranged in the shape of a chain on a steel thread (K. Klemm: Gentamcin-PMMA-beads in treating bone and soft tissue infections. Zentralbl. Chir. 104(14) (1979) 934-942.; K. Klemm: Antibiotic bead chains. Clin. Orthop. 295 (1993) 63-76.). The chain-shaped active ingredient carrier (Septopal®) has proved effective in local antibiotic treatment of osteomyelitis for decades. One advantage is that gentamicin sulfate is released from the active ingredient carrier in large amounts over a period of several days. A further advantage is that the chain-shaped active ingredient carrier can be easily adjusted to the anatomical situation at the implantation location by the medical user by simply cutting the steel thread with surplus beads. A drawback is that the active ingredient carrier only contains gentamicin sulfate and that the medical user cannot modify the active ingredient carrier with other antibiotics, according to the sensitivity of the microbes. In addition, once the bead chain has been implanted, the administration of the pharmaceutical active ingredient can no longer be adjusted to the progression of the treatment without replacing the bead chain. As a result, it is in particular not possible, or only possible to a limited extent, to successfully locally treat infections with problem germs, such as MRSA and VRSA. The removal of the bead chains once the active ingredient has been released entails considerable strain on the patient due to intergrowth with connective tissue.

Nonwovens and sponges made of collagen or gelatin are examples of resorbable or biodegradable active ingredient carriers. Examples are mentioned in DE 34 29 038 A1, DE 33 34 595 A1, DE 28 43 963 C2, DE 32 03 957 C2 and DE 33 34 595 A1. The carriers contain gentamicin sulfate or mixtures of gentamicin sulfate and a gentamicin salt that is sparingly soluble in water. Furthermore, there are a large number of resorbable or biodegradable active ingredient carriers based on tricalcium phosphate, hydroxyapatite, gypsum and mixtures thereof, as well as composite materials consisting of the salts and organic binders. An overview was published by Kuhn et al. (K.-D. Kühn, N. Renz, A. Trampuz: Lokale Antibiotika-Therapie. Der Unfallchirurg. 120 (2017) 561-572).

A drawback to the mentioned non-resorbable and resorbable or biodegradable active ingredient carriers is that the antimicrobial active ingredient is fixed by the selected composition and that the active ingredient can no longer be replaced or supplemented with other active ingredients once the active ingredient carrier has been implanted. Furthermore, with all existing local active ingredient delivery systems, the release of the active ingredient is based on the principle of diffusion, and thus only in the first few hours or at most the first few days are high amounts of the active ingredient released. One exception is the use of active ingredient salts that are sparingly soluble in water, for which active ingredient release depends on the solubility equilibrium of the active ingredient salts.

Therefore, a desirable active ingredient carrier is one which allows any desired pharmaceutical active ingredients to be locally applied and in which the pharmaceutical active ingredient can be replaced with other fluid pharmaceutical active ingredients at any time. Furthermore, it is desirable for the active ingredient concentration achieved directly at the implantation location to be directly adjustable from the outside. EP 1 932 560 B1 discloses a catheter for applying a medical liquid. The catheter has a tube which, at the distal tube end thereof, has a plurality of openings through which a liquid can be applied from the inside of the tube. Further similar catheters are known from U.S. Pat. No. 5,800,407 A1, U.S. Pat. No. 6,537,194 A1 and U.S. Pat. No. 5,425,723 A1. The catheters have the drawback of having a fixed length over which the catheters can administer the medical liquid, and are therefore only usable for particular applications and treatment situations with particular geometric dimensions. The catheters therefore cannot be readily changed to be adjusted to the treatment situation. In addition, the administration of the medical liquid can only be adjusted by a slowly diminishing pressure, the pressure depending on the elasticity of the catheter walls containing the liquid. It is not possible to administer the medical liquid quickly and at short notice. Furthermore, when the catheter is used for a longer period (of more than one day), the tissue surrounding the catheter may grow into the openings and thus cause significant problems when the catheter is pulled out/removed. The surrounding tissue can therefore be damaged by the removal of the catheter and thus impair the success of treatment.

Unpublished document EP 19 198 038 describes a device for temporarily, locally applying medical fluids that has a tube that can be shortened on the distal side thereof. This may present a drawback if the distal closure cannot be readily inserted into the tube. At the same time, however, the medical liquid is intended not to flow out outside the hollow space intended for treatment.

For these and other reasons there is a need for the present invention.

SUMMARY

One embodiment relates in particular to a medical device for temporarily, locally applying pharmaceutical fluids or other medical fluids over a period of hours to several days. The length of the device according to one embodiment can be adjusted by mechanical shortening, depending on the particular geometric requirement or depending on the anatomical situation of the implantation location, without a loss of function being incurred. Furthermore, a device for continuously outputting medical fluids is proposed that can advantageously be combined with the device for locally applying medical fluids such that pharmaceutical fluids or other medical fluids can be continuously locally applied over a period of hours to days.

BRIEF DESCRIPTION OF THE DRAWINGS

Further example embodiments of the embodiment are explained below with reference to eighteen schematic figures, but without thereby restricting the embodiment. In the drawings.

DETAILED DESCRIPTION

Figure 1:
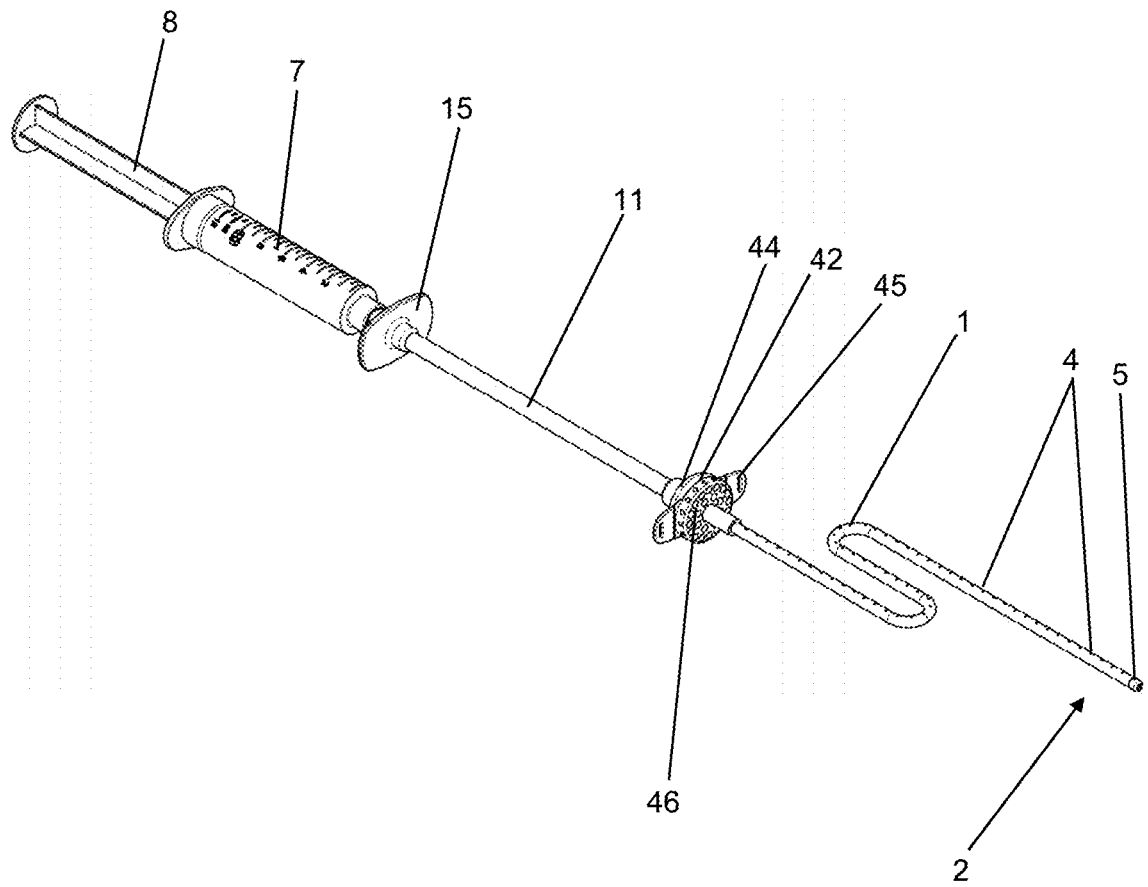
FIG. 1: is a schematic perspective view of a first example device according to the embodiment for locally applying a fluid.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

The object of one embodiment is to overcome the drawbacks of the prior art. In particular, it is intended to provide a device for locally applying medical fluids, in particular pharmaceutical fluids, such as antibiotic solutions, that allows the medical fluid to be locally and temporarily administered in regions with poor access, such as in hollow spaces of non-implanted implants or other medical devices. The device is intended to be easily adjustable to different areas of use. The walls of the hollow spaces to be flushed are intended to be prevented from being mechanically strained as far as possible. In the case of the use for treating an infection, it is intended to be possible to provide as non-invasive a treatment as possible in which the adjacent infected tissue is irritated as little as possible, both when the fluid is being temporarily administered and when the inserted portion of the device is inserted and removed. The device is also intended to be suitable for repeated administration of the fluid at a particular location over longer periods, without the device having to be removed for this purpose. The device is intended to be inexpensive to manufacture and to be in one embodiment a hygienic disposable product that can only be used once. It is intended for at least the portion of the device that can be placed in the hollow space to be flushed, or the entire device, to be easily and inexpensively disposable. At the same time, however, the medical liquid is intended not to flow out outside the hollow space intended for treatment.

The object of one embodiment is therefore also to develop a simple, inexpensive device for locally applying medical fluids. The device is intended in particular to allow pharmaceutical fluids of any desired composition, for example antibiotic solutions, to be locally applied. In a medical use after implantation, a portion of the device is positioned in the patient, and a second portion of the device is positioned outside the patient. The medical fluids are intended to be capable of being introduced in the portion of the device located outside the patient and of being guided to and released at the implantation location by the device. The device is intended to be plastically deformable in order to be able to adapt to the anatomical characteristics at the implantation location or the geometric shape of the cavity. After completion of shaping by the medical user, the shape of the device is intended not to be able to change, except by manual deformation by the medical user.

Pharmaceutical fluids are intended to be released from openings arranged along the device. The openings are intended to be reversibly closable in order to prevent the back flow of contaminated fluid into the inside of the device or prevent the ingrowing of connective tissue or clogging of the openings with coagulated blood. Furthermore, the device is intended to be designed such that the portion of the device possibly located in the patient can be adjusted to the particular anatomical situation of the patient by shortening the length, without the function of the device being impaired. The shortening is intended to take place such that the proximal side of the device not located in the patient can be shortened.

Moreover, the shape and diameter of the device should not change significantly when the medical fluid or the pharmaceutical fluid is applied. Significant transverse elongation could otherwise cause the patient pain at the inflamed or infected tissue. Furthermore, it is intended to develop a simple, inexpensive device that allows a continuous output of medical fluids, in particular pharmaceutical fluids, over a period of hours to days, without the need for electric motors, batteries or accumulators.

The object of one embodiment is achieved by a device for locally applying a medical fluid, including
  a tube, the tube being flexibly deformable and including a tube wall,
  wherein the tube includes a plurality of openings in the tube wall, the plurality of openings connecting an inner line of the tube to the surroundings of the tube, and the tube being closed at a distal tube end of the tube,
  wherein a proximal tube end of the tube is liquid-permeably connected or connectable to a container for the medical fluid such that the medical fluid can be pushed from the container through the proximal tube end of the tube into the inner line of the tube and can be pushed out through the plurality of openings into the surroundings of the tube,
  wherein the device includes an outer sleeve for fluid-tightly closing a subset of the plurality of openings, the outer sleeve being axially movably arranged around the tube, and the outer sleeve being shorter than the tube such that the distal openings that are not part of the closed subset of the plurality of openings are exposed.

In one embodiment, the closed subset of the plurality of openings is a proximal subset of the plurality of openings. The closed subset of the plurality of openings is therefore in one embodiment on the proximal side of the tube.

The device also allows medical instruments and non-implanted implants to be rinsed or flushed out, in particular medical instruments and implants having hollow spaces into which the tube can be inserted. However, the device can also be used to freely distribute the medical fluid. Particularly suitable is a medical use of the device according to the embodiment in which the tube is inserted into a cavity in the human body, and the fluid is used to treat the adjacent tissue.

The device according to one embodiment a medical device.

The outer sleeve is in one embodiment an outer tube or an outer pipe for fluid-tightly closing a proximal subset of the plurality of openings.

In the distal tube end of the tube, in particular in a closure element by using which the tube is fluid-tightly closed at the distal tube end of the tube, at least one distal opening may be arranged. The medical fluid can also be applied via the at least one distal opening.

The tube is in one embodiment plastically deformable.

It may be provided that the outer sleeve has an inner diameter that is greater than or equal to the outer diameter of the tube. The sleeve in one embodiment has a cylindrical inner face.

According to a preferred further development of one embodiment, it may be provided that a non-return valve is arranged in the proximal side of the tube.

It may further be provided that a valve element, in particular a non-return valve, is arranged in the region of the proximal tube end of the tube or in the connection to the container for the medical fluid, the valve element preventing the flow of the medical fluid towards the container and the flow of the medical fluid from the container towards the distal portion.

This ensures that contaminated medical fluid does not penetrate the container for the medical fluid from the inner line.

In the present case, the directional references "distal" and "proximal" refer to the intended flow direction of the medical fluid while in use. Here, the medical fluid flows from a proximal tube end of the tube towards the distal tube end of the tube and then out of the plurality of openings.

The tube wall may be in the form of a jacket.

The directional information "axial" refers to the axis of symmetry of the tube when the tube is straight.

The tube is in one embodiment cylindrical except for the plurality of openings. The tube wall thus in one embodiment defines the tube on the cylindrical circumferential surface thereof. In the case of straight tubes having a cylindrical geometry, the circumferential surface is the wall perpendicular to the cylinder axis of the cylindrical tube. The openings are therefore located in the circumferential surface.

A pharmaceutical fluid is in one embodiment used as the medical fluid. A pharmaceutical fluid contains at least one pharmaceutical active ingredient. Solutions containing at least one antibiotic, at least one cytostatic agent, at least one chemotherapeutic agent and/or at least one antimycotic agent are particularly preferred as pharmaceutical fluids or medical fluids. Alternative medical fluids may contain disinfecting components. The term "pharmaceutical fluid" is therefore understood to mean aqueous and non-aqueous solutions and suspensions of pharmaceutical active ingredients. Furthermore, the term "pharmaceutical fluid" is also understood to mean mixtures and solutions of gases in water, water-containing liquids and non-aqueous liquids. The term "pharmaceutical fluid" in one embodiment also includes gases and gas mixtures.

It may also be provided that at least one of the openings is arranged in the region of the distal tube end of the tube, in one embodiment within 5 mm of the distal tube end of the tube, in one embodiment within 3 mm of the distal tube end of the tube.

In one embodiment, at least three openings are arranged in the tube wall as the plurality of openings.

It may also be provided that all, pairs or groups of the plurality of openings are spaced apart from one another in the axial direction of the outer tube.

As a result, the medical fluid can emerge at various axially spaced points. In addition, the tube can be shortened lengthways on the proximal side, with at least one of the plurality of openings still present in a distal portion of the tube.

The outer sleeve has an inner diameter that is greater than or equal to the outer diameter of the tube.

The outer sleeve has a shorter length than the tube.

The outer sleeve in one embodiment has a length of 10 to 15 cm. In typical anatomical circumstances, the length is sufficient to cover the openings of the tube located below the outer sleeve, from a tubular bone to above the overlying soft tissue layer, in such a way as to prevent undesired escape of the pharmaceutical fluid outside the tubular bone to be treated and the surface of the skin.

It may be provided that the tube wall includes an outer wall that is made of a first material and is arranged radially externally, and the tube wall includes an inner wall that is made of a second material, is arranged radially internally and delimits the inner line of the tube.

The different materials allow the tube to be designed as a composite material, the outer wall and the inner wall being able to respond differently to physical or chemical parameters, such as a pressure or temperature, such that certain desired changes in properties, such as the shape and rigidity of the tube, can be set as a response to a change in the physical or chemical parameters. As a result, when the first and second materials are appropriately selected, the plurality of openings passing through the tube wall can be opened and closed by a changeable hydrostatic pressure, for example.

The first material and the second material differ in one embodiment with regard to at least one material property. In one embodiment, the first material and the second material differ with regard to elasticity and/or hardness.

According to one embodiment, the second material may be a rubber-elastic material, while the first material is more dimensionally stable than the second material. For example, the inner wall may be a coating of a rubber-elastic material on the inside of the outer wall.

The outer wall may surround the inner wall in the manner of a jacket.

In devices having an outer wall and an inner wall, it may also be provided that the outer wall and the inner wall are rigidly interconnected, in one embodiment interconnected over the entire surface.

Thus, the outer wall and the inner wall are fixed in relation to one another. It is thus possible for the plurality of openings in the inner wall to close as a result of elastic tension being released in the absence of pressurization of the medical fluid in the inner line, while the outer wall can absorb the pressure required to open the plurality of openings in the inner wall.

Furthermore, it may be provided that the plurality of openings in the outer wall of the tube wall are open irrespective of the pressure of the medical fluid, while the openings in the inner wall of the tube wall are closed without pressure being applied by the medical fluid and are liquid-permeably openable by using pressure on the medical fluid.

As a result, the plurality of openings in the tube wall close when a medical liquid is not pushed into the inner line. In an alternating operation, tissue can thus be prevented from growing into the inner line through the plurality of openings, and the device is thereby prevented from intergrowing in the cavity.

In one embodiment, it may also be provided that the outer wall of the tube wall absorbs pressure of the medical fluid in the inner line, transmitted via the inner wall of the tube wall, without radially expanding by more than 5%, in one embodiment without radially expanding by more than 1%.

Under normal conditions in normal uses of the device according to one embodiment, the pressure of the medical fluid cannot exceed 500 kPa. It may therefore be provided that the outer wall of the tube wall absorbs hydrostatic pressure, transmitted via the inner wall of the tube wall, of at most 500 kPa in the inner line, without radially expanding by more than 5%, in one embodiment without radially expanding by more than 1%.

This ensures that the tube does not expand too greatly when the medical fluid is pushed through the tube. This prevents irritation of the surrounding tissue or mechanical strain on the surrounding structures.

It may also be provided that the first material has a larger Shore A hardness than the second material, the first material in one embodiment having a Shore A hardness of more than 60, and the second material in one embodiment having a Shore A hardness of less than 60.

For this purpose, the Shore hardness is determined in accordance with DIN ISO 7619-1 (2012-02) [2]. Using materials having the difference in hardness ensures that the inner wall can close the plurality of openings in the outer wall.

It may further be provided that the plurality of openings in the inner wall have an open cross section which, when hydrostatic pressure of 500 kPa is applied by the medical fluid, is larger by a factor or two or more than when pressure is not applied.

This ensures that the plurality of openings in the inner wall can be opened by the pressure of the medical fluid.

It may be provided that the plurality of openings in the inner wall or the outer wall are slot-shaped.

Both of these measures allow the slot-shaped openings to be opened by pressure acting on the medical fluid and to close again when the pressure on the medical fluid is reduced. As a result, growing of tissue into the plurality of openings can be avoided in an alternating operation. It is thus also possible to prevent contamination of the medical fluid in the inner line. The plurality of openings in the inner wall are in one embodiment slot-shaped. This is advantageous in that the deformation thereof does not cause the outer surfaces of the tube to be deformed.

Furthermore, it may be provided that the plurality of openings in the tube in the outer wall have a diameter of at most 500 μm, in one embodiment at most 250 μm, and particularly in one embodiment at most 100 μm.

The diameter refers to the average diameter of the open cross section of the plurality of openings. If the inner wall is designed to close the plurality of opening in the relaxed state, i.e. when pressure is not applied, the diameter of the inner wall is naturally smaller in the closed state at least. In the open state of the plurality of openings in the inner wall, the diameter of the plurality of openings in the inner wall is at most as large as the diameter of the plurality of openings in the outer wall.

With openings having such maximum diameters, it is ensured that the flow rates of the medical fluid are not too high and the open line cross section of the inner line is sufficient to also be able to use the openings close to the distal tube end of the tube only for administering the medical fluid.

Embodiments may also be distinguished in that the tube is formed of a coaxial coextrudate, the inner wall consisting of a rubber-elastic polymer, in particular polyurethane or a weakly crosslinked polymer, and the outer wall consisting of a non-rubber-elastic thermoplastic polymer or of a strongly crosslinked polymer, in particular polyamide.

As a result, the openings are closed by the inner wall when hydrostatic pressure is not exerted on the inner wall, and the openings in the inner wall open when the pressure exerted by the medical fluid increases. In this way, ingrowing of tissue and contamination of the inner line via the openings can be prevented.

Coextruded tubes in which the inner wall consists of a rubber-elastic polyurethane and the outer wall is formed of thermoplastic, non-rubber-elastic polyamide are particularly preferred. The plurality of openings pass through the inner wall and the outer wall. When pressure is applied by a medical fluid, the openings in the inner wall are unblocked by the elastic polyurethane elastically yielding, and the medical fluid can escape from the outer wall through the openings in the stiff polyamide. After the discharge of fluid is complete, the openings in the inner wall of the tube close again, and bodily fluids, such as blood or wound exudate, cannot penetrate the inner line of the tube. While fluid is being discharged, the stiff, non-elastic outer wall prevents radial expansion of the tube. As a result, forces are not exerted on the tissue to be treated, and pain due to mechanical force is prevented, or forces are not transferred to the walls of the flushed implant or hollow space.

In devices according to one embodiment having an inner wall and an outer wall, it may be provided that the plurality of openings in the inner wall can be reversibly fluid-tightly closed depending on a physical variable acting on the second material, in particular depending on pressure acting on the second material from the medical fluid.

In one embodiment, it may be provided that the plurality of openings in the outer wall can be reversibly fluid-tightly closed depending on a physical variable acting on the first material, in particular depending on pressure acting on the first material from the medical fluid.

In the second case, the pressure in the open parts of the plurality of openings in the inner wall can act on the first material of the outer wall. In one embodiment, the first material and the second material are selected such that the plurality of openings in the inner wall can be reversibly fluid-tightly closed depending on a physical variable acting on the second material, in particular depending on a pressure acting on the second material from the medical fluid, or the plurality of openings in the outer wall can be reversibly fluid-tightly closed depending on a physical variable acting on the first material, in particular depending on a pressure acting on the first material from the medical fluid.

These measures allow the plurality of openings to be reversibly opened and closed. In addition to pressure, electrical or mechanical tension, a magnetic field or temperature (for example, using shape memory alloys) may be used to open and close the plurality of openings, for example.

Furthermore, it may be provided that the plurality of openings can be reversibly opened by elastic deformation of the second material, while the plurality of openings in the first material remain open, the first material in one embodiment being dimensionally stable such that the outer wall absorbs at least some of the forces caused by the elastic deformation of the second material and thus counteracts radial deformation of the tube.

As a result, the tube does not radially deform or radially deforms only to a very small extent.

Alternatively, it may also be provided that the plurality of openings can be reversibly opened by elastic deformation of the first material, while the plurality of openings in the second material remain open, the second material in one embodiment being dimensionally stable such that the inner wall absorbs at least some of the forces caused by the elastic deformation of the first material and thus counteracts radial deformation of the tube.

As part of one embodiment, it is also proposed for the device to include a closure element, by using which the tube is fluid-tightly closed at the distal tube end of the tube.

The design of the device is thus simplified. The closure element can mechanically close the tube and produce a seal by tensioning the tube.

It may also be provided that the inner line of the tube starts at a proximal opening in the proximal tube end of the tube and ends at a distal opening in the distal tube end of the tube, the distal opening of the tube in one embodiment being closed by the closure element.

The inner line can thus connect the two open ends, i.e. the distal tube end and the proximal tube end of the tube. As a result, the medical fluid can be guided through the inner line of the tube and applied through the plurality of openings in the tube wall.

In one embodiment, the closure element is screwed or pushed into the distal tube end of the tube such so as to completely liquid-tightly and particularly in one embodiment also gas-tightly close the inner line over the entire cross section thereof at the distal tube end.

Furthermore, it may be provided that the tube is gas-tightly and/or pressure-tightly closed or closable by the closure element at the distal tube end.

It may further be provided that the device includes the container for the medical fluid, the container in one embodiment including a hollow cylinder having a piston that is axially movable in the hollow cylinder and closes a first end of the hollow cylinder, the hollow cylinder including an output opening at an end opposite the first end, the output opening being connected or connectable to the proximal tube end of the tube, in one embodiment being connected or connectable to the proximal tube end of the tube via a manually operable valve element for regulating the flow rate of the medical fluid.

As a result, a separate reservoir for the medical liquid does not have to be connected to the device. The piston may in one embodiment be driven by at least one tensioned resilient spring.

It may also be provided that a medical fluid, in particular a pharmaceutical fluid, is contained in the container.

As a result, the device can be used directly to generate a flow of the medical fluid from the plurality of openings.

According to one embodiment, it may be provided that the device includes a conveying device, by using which the medical fluid can be pushed out of the connected or connectable container into the tube, through the inner line of the tube and through the plurality of openings into the surroundings of the tube.

Thus, the device can also be used to drive the current of the medical liquid. A device of this kind allows pharmaceutical fluids to be locally applied over a period of hours to several days, without the need for complex electrically driven pumping systems. In one embodiment, the conveying device allows the medical fluid to be discontinuously or continuously conveyed.

In devices having a conveying device, it may in one embodiment be provided that the conveying device includes an energy storage element, in particular at least one tensioned spring, the conveying device being drivable with energy from the energy storage element, the energy storage element in one embodiment allowing a piston to be driven in a hollow cylinder as the container, towards an opposite output opening.

As a result, the device does not have to be connected to an external energy supply to drive the conveying device. A tensioned spring contains enough energy to push out an amount of a few milliliters to a few centiliters of the medical fluid by using the device.

It may further be provided that the device includes a connector for connecting the tube to the container for the medical fluid, the connector including a conical or cylindrical projection that is inserted or screwed into the tube such that the tube is tensioned by the conical or cylindrical projection in the region of the proximal tube end of the tube such that the tube is fluid-tightly connected to the container at the proximal tube end of the tube and rigidly connected to the outer sleeve.

This allows the proximal tube end of the tube to be reliably sealed even after a proximal portion of the tube has been shortened.

It may be provided that the conical or cylindrical projection includes ribs on the outside of the conical or cylindrical projection, or the conical or cylindrical projection includes an outer thread, the outer thread or the conical or cylindrical projection having a larger outer diameter than the inner diameter of the tube.

According to one embodiment, it may be provided that the tube is plastically deformable and has an outer diameter smaller than or equal to 7 mm, in one embodiment an outer diameter of between 2 mm and 4 mm.

Owing to the small outer diameter, the tube can be easily inserted into cavities of implants and in cavities in the human body and is suitable here for flushing out the cavities. The plastic deformability prevents elastic force from acting on the walls of the hollow space to be flushed and from mechanically straining the hollow space.

Furthermore, it may be provided that an X-ray-opaque material is contained in the tube at least at the distal tube end of the tube and/or in the closure element, an X-ray-opaque material in one embodiment being contained in a distal portion of the tube and, if present, in the closure element, particularly in one embodiment being contained over the entire length of the tube and, if present, in the closure element.

In this way, the position of the tube can be made visible by X-ray processes, the tube can be monitored by X-ray, and the position of the device in the patient can thus be clearly determined from X-ray images.

The X-ray-opaque material may in one embodiment be selected from stainless steel, titanium, titanium alloys, tantalum, tantalum alloys, barium sulfate, plastics materials containing barium sulfate, zirconium dioxide and plastics materials containing zirconium dioxide.

It may further be provided that at least one metal wire, at least one metal coil and/or at least one metal mesh is or are arranged in the inner line of the tube and/or in the tube wall of the tube, the at least one metal wire, the at least one metal coil and/or the at least one metal mesh in one embodiment being arranged along the entire length of the tube.

The at least one metal wire, the at least one metal coil and the at least one metal mesh conduce to the plastic deformability of the tube. In this way, the shape of the tube can be changed and thus adjusted to the particular situation, without the surroundings of the device being mechanically stressed, the shape of the tube being maintained by the at least one metal wire, the at least one metal coil and/or the at least one metal mesh. In this way, having been previously shaped to fit the anatomical circumstances, the device maintains its shape. It is thus possible to apply pharmaceutical fluids to precisely predetermined implantation locations in a positionally precise manner. In addition, the metal structures in the X-ray are distinguishable in the X-ray image.

It may in one embodiment be provided that an X-ray-opaque material is contained in the closure element or that the closure element consists of an X-ray-opaque material. The X-ray-opaque material may in one embodiment be selected from stainless steel, titanium, titanium alloys, tantalum, tantalum alloys, barium sulfate, plastics materials containing barium sulfate, zirconium dioxide and plastics materials containing zirconium dioxide.

It may in one embodiment be provided that the total of the open cross-sectional areas of all of the plurality of openings is at most as large as the open cross section of the inner line.

This ensures that the medical fluid can also flow through those openings among the plurality of openings that are arranged at the distal tube end of the tube. This ensures that medical fluid also flows out of the openings arranged at the distal tube end. The total of the free cross-sectional areas of all of the plurality of openings refers to the open state of the plurality of openings.

As part of one embodiment, it is also proposed that with an internal pressure of 500 kPa, the tube radially expands by at most 10%, in one embodiment by at most 5%, in relation to normal pressure.

This ensures that the tube does not expand too greatly when the medical fluid is pushed through the tube. This prevents irritation of the surrounding tissue or mechanical strain on the surrounding structures.

It may in one embodiment also be provided that the closure element includes the following features: a rotationally symmetric first body having an outer thread or having ribs extending around the periphery, the outer thread or the ribs having a larger outer diameter than the inner diameter of the tube; a rotationally symmetrical second body having an outer diameter that is smaller than or equal to the outer diameter of the tube, the axial extension of the second body being at least 5 mm, the rotationally symmetrical first body being axially connected to the rotationally symmetrical second body.

In this way, the tube can be reliably and liquid-tightly closed by the closure element.

It may also be provided that the closure element is screwed or pushed into the distal tube end of the tube and completely liquid-tightly and gas-tightly closes the open cross section of the inner line of the tube at the distal tube end.

This ensures that sufficient pressure can be built up in the inner line by the medical fluid in order to be able to push the medical liquid out of all of the plurality of openings. The closure element in one embodiment also gas-tightly closes the distal tube end of the tube.

The objects one embodiment are also achieved by a method for adjusting the tube length of a medical device for locally applying a medical fluid, the device including a tube having a tube wall, the tube including a plurality of openings in the tube wall, the plurality of openings connecting an inner line of the tube to the surroundings of the tube, and the device including an outer sleeve for fluid-tightly closing a proximal portion of the plurality of openings and being axially movably arranged around the tube, and the outer sleeve being shorter than the tube such that the openings that are not part of the proximal subset of the plurality of openings are exposed, the method including the following steps:

A) moving the outer sleeve on the tube until a desired distal length of the tube is exposed;
B) cutting the proximal portion of the tube protruding beyond the outer sleeve;
C) fixing the outer sleeve in relation to the tube; and
D) connecting the new proximal tube end of the tube to a container for the medical fluid or to a connection for a container for the medical fluid such that the container is liquid-permeably connected or connectable to the inner line of the tube.

The steps are in one embodiment carried out chronologically one after the other.

In this way, the tube can be easily shortened to a length suitable for use.

In the method according to the embodiment, it may be provided that in the method, no medical treatment of a human or animal body takes place, and/or the medical fluid is not administered to a human or animal body as part of the method.

This is to clarify that the method according to one embodiment is not a method for treating the human body.

The objects of one embodiment are also achieved by a method for operating a medical device for locally applying a medical fluid, including a method according to one embodiment for adjusting the tube length of a medical device for locally applying a medical fluid, wherein the tube wall of the tube of the device includes an outer wall that is made of a first material and is arranged radially externally, and the tube wall has an inner wall that is made of a second material, is arranged radially internally and delimits the inner line of the tube, characterized by the following steps:

Step E) introducing a medical fluid into the tube;
Step F) exerting pressure onto the medical fluid in the tube;
Step G) opening the plurality of openings in the inner wall or in the outer wall of the tube by using the pressure of the medical fluid acting on the plurality of openings (4); and
Step H) driving out medical fluid through the opened plurality of openings.

Following step H), the pressure on the medical fluid can be reduced, and the plurality of openings can be thereby closed.

Furthermore, it may be provided that a subsequent optional step I) takes place: Step I) reducing the pressure on the medical fluid in the tube after step H) and thereby closing the plurality of openings in the inner wall of the tube or decreasing the open cross section of the plurality of openings in the inner wall of the tube.

In this way, the method can be used in an alternating manner, without the medical fluid in the inner line being contaminated by backflowing fluids.

According to one embodiment, it may be provided that the method is carried out by a device according to one embodiment.

As a result, the advantages mentioned in relation to the relevant claims apply to the method.

One embodiment is based on the surprising finding that the tube can be easily shortened and the length thereof can thus be adjusted to the particular situation, even if the distal tube end of the tube is already located in the hollow space in which the medical fluid is intended to be applied. For this purpose, the proximal tube end of the tube simply has to be connected, after being cut, to an available connector or to another connection to the container for the medical fluid. Escape through openings in the tube that are not arranged within the hollow space is prevented by the outer sleeve closing the external openings of the plurality of the openings that are arranged on the proximal side of the tube. By widening the tube on the proximal side by inserting a connector or another widening connection, the outer wall of the outer tube can be pressed against the inner wall of the outer sleeve, thus producing a fixing and sealing function.

The device allows medical instruments and non-implanted implants to be rinsed or flushed out, in particular medical instruments and implants having hollow spaces into which the tube can be inserted. However, the device can also be used to freely distribute the medical fluid. Particularly suitable is a medical use of the device according to one embodiment in which the tube is inserted into a cavity in the human body, and the fluid is used to treat the adjacent tissue.

A further surprising effect of one embodiment can be considered to be that a tube having an inner wall and an outer wall made of different materials makes it possible to reversibly open and close the plurality of openings in the tube wall, depending on the pressure of a medical fluid or depending on other physical state variables, effects or fields, in order to temporarily administer a medical fluid. As a result of the effect on only the inner wall or only the outer wall of the tube, the plurality of openings can be opened or closed. Meanwhile, forces are not exerted on the outer wall, or deformation of the outer shape of the tube is avoided. In this way, the tube remains externally dimensionally stable. Mechanical stress on the adjacent surfaces to be treated with the fluid is thus avoided. The thus provided valve can thus be opened and closed again without changing the outer shape of the tube. In this way, mechanical irritation of adjacent infected tissue can be prevented or at least reduced, for example. In particular, if the plurality of openings are only liquid-permeably open when the openings are opened by the pressure of the medical fluid, the plurality of openings and thus the device are closed without further supply of the medical fluid.

The device can be inexpensively produced entirely or largely from plastics material and can thus be made available as a hygienic disposable product. The plurality of openings in the tube are closed such that in the closed state, undercuts in the space between the outer wall and the inner wall are not formed, into which tissue could grow, thereby making it difficult to remove the device or the tube.

The device in one embodiment has a valve function that can be operated outside the patient. The length of the device according to one embodiment can be adjusted by simple mechanical shortening, depending on the anatomical situation of the implantation location or depending on the depth of the hollow space, without a loss of function being incurred. This is simplified by it being possible to shorten the tube on the proximal side when the distal side is already arranged inside the hollow space to be flushed.

The particular advantage of the device according to one embodiment is that the medical user can apply any desired medical fluid of a precisely defined volume. In fluids containing active ingredients, one or more pharmaceutical active ingredients in the fluid can be set to precisely predetermined concentrations. This makes it possible to achieve precisely defined concentrations of active ingredients in the immediate vicinity of the openings in the device and to use the same for treatment. A further advantage of the device according to one embodiment is that the plurality of openings in the tube are only open during application and are closed thereafter, meaning that blood or tissue fluid and any connective tissue that forms cannot penetrate the space between the inner wall and the outer wall and form undercuts that tear when the device is removed and thus cause fresh irritation of the tissue that has just been treated. In addition, blockages of the device, in particular the openings in the tube, are avoided.

A further advantage of the device according to one embodiment is that any desired cavities in the human organism can be treated with pharmaceutical fluids of any desired composition. The length and shape of the device can be adjusted in a customized manner. Pharmaceutical fluids having precisely set active ingredient concentrations can be applied. As a result, it is also possible, for example, to treat bone cavities infected with multiresistant microorganisms by locally applying antibiotic mixtures.

An example device according to one embodiment for locally applying fluids and having a valve function is made up of
 a) a flexibly deformable first tube, at least two openings being made in the circumferential surface of the first tube, the openings connecting the interior of the first tube to the surroundings, the total of the cross-sectional areas of the openings being smaller than or equal to the inner cross section of the first tube,
 b) a closure element that liquid-tightly and gas-tightly closes the distal end portion of the first tube,
 c) a second tube (as the outer sleeve) that surrounds the first tube and is axially movable on the first tube, the second tube being arranged at the proximal tube end of the first tube, and
 d) a connector that is screwed or pushed into the proximal tube end of the first tube, the connector pressing the first tube against the inner wall of the second tube such that liquid cannot escape between the proximal tube end of the first tube and the proximal tube end of the second tube, the connector being liquid-penetrable and being liquid-tightly connectable or connected to an active ingredient reservoir that discontinuously or continuously conveys active ingredient solution.

For example, the closure element is made up of a first rotationally symmetrical body having an outer thread, the outer thread having a larger outer diameter than the inner diameter of the tube, and of a second rotationally symmetrical body having an outer diameter that is smaller than or equal to the outer diameter of the outer tube, the axial extension of the second rotationally symmetrical body being at least 5 mm, and the first rotationally symmetrical body being axially connected to the second rotationally symmetrical body.

In a further alternative embodiment, an example closure element is made up of a first rotationally symmetrical body having ribs extending around the periphery, the ribs having a larger outer diameter than the inner diameter of the inner tube, and of a second rotationally symmetrical body having an outer diameter that is smaller than or equal to the outer diameter of the outer tube, the axial extension of the second rotationally symmetrical body being at least 5 mm, and the first rotationally symmetrical body being axially connected to the second rotationally symmetrical body.

A combination of the device for locally applying pharmaceutical fluids with a device for continuously pushing out fluids is advantageous. The combined device is made up of
 a) a flexibly deformable tube, at least two openings being made in the circumferential surface, the openings connecting the interior of the tube to the surroundings, the total of the cross-sectional areas of the openings being smaller than or equal to the inner cross section of the tube,
 b) a closure element that liquid-tightly and gas-tightly closes the distal end portion of the tube,
 c) an outer sleeve that surrounds the tube in regions and is axially movable on the tube, the outer sleeve being arranged at the proximal tube end of the tube, and
 d) a connector that is screwed or pushed into the proximal tube end of the tube, the connector pressing the tube against the inner wall of the outer sleeve such that liquid cannot escape between the proximal tube end of the tube and the proximal end of the outer sleeve, the connector being liquid-permeably connected to a device for continuously outputting pharmaceutical fluids, the device for continuously outputting pharmaceutical fluids being made up of
 e) a hollow cylinder in which a pharmaceutical fluid is located,
 f) a piston that is axially movable in the hollow cylinder and closes one end of the hollow cylinder,
 g) at least one liquid-penetrable output opening in the closed head of the hollow cylinder,
 h) a spring element that is connected to the axially movable piston,
 i) the tensioned spring element moving the piston towards the output opening, and
 j) the pharmaceutical fluid in the hollow cylinder being pushed through the output opening and through the connector into the proximal tube end of the tube.

It is advantageous according to one embodiment for a valve element to be arranged between the output opening and the connector. It is thereby possible to control the volumetric flow of the pharmaceutical fluid. A device of this kind allows the pharmaceutical fluid to be locally applied over a period of hours to several days, without the need for complex electrically driven pumping systems.

In the drawings and in the following description of the example embodiments that are explained with reference to the drawings, the same reference signs are in some cases used for the same or similar parts across different example embodiments in order to make it easier to compare the example embodiments and to improve readability.

Figure 6:
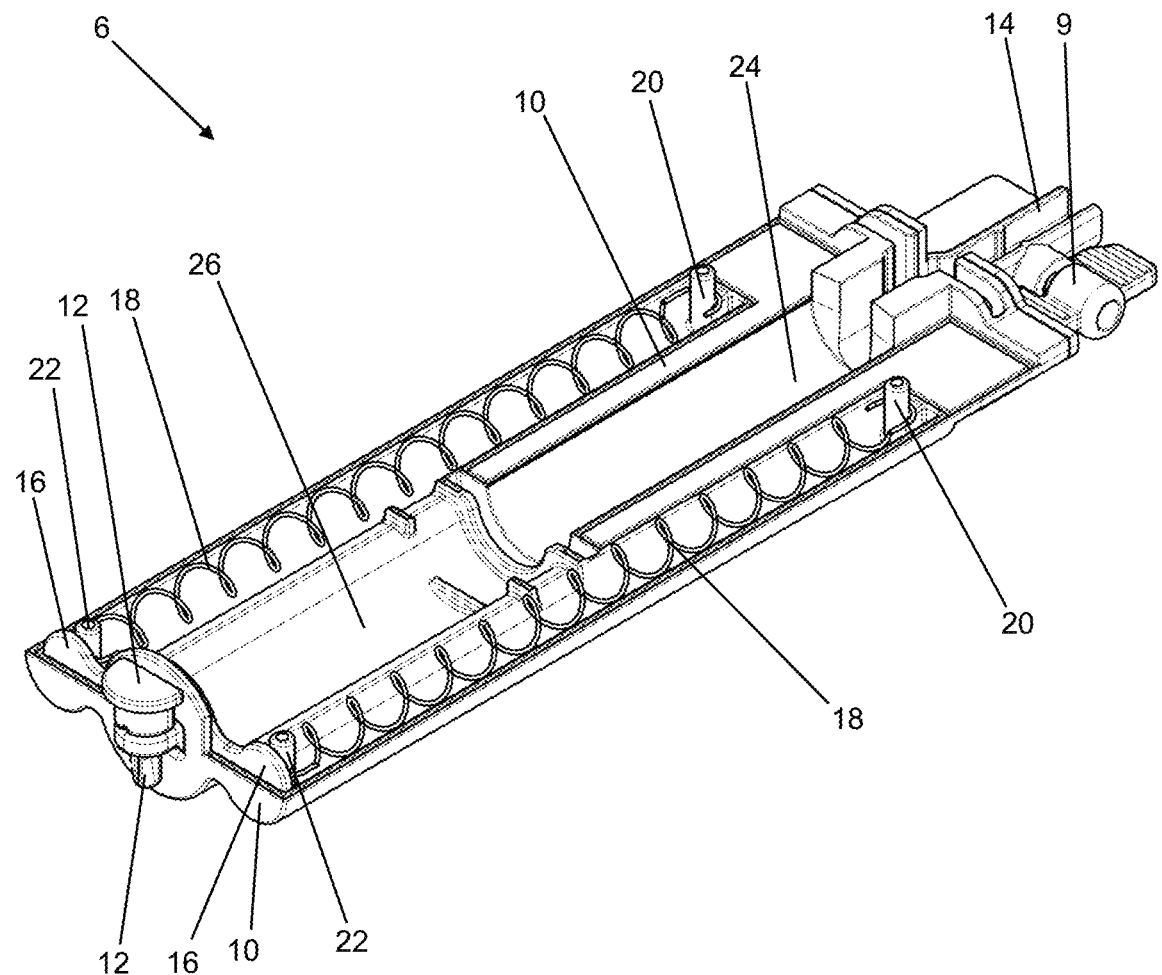
FIG. 6: is a schematic perspective partial cross-sectional view of a conveying device for the container of a device according to FIGS. 1 to 5.
Figure 7:
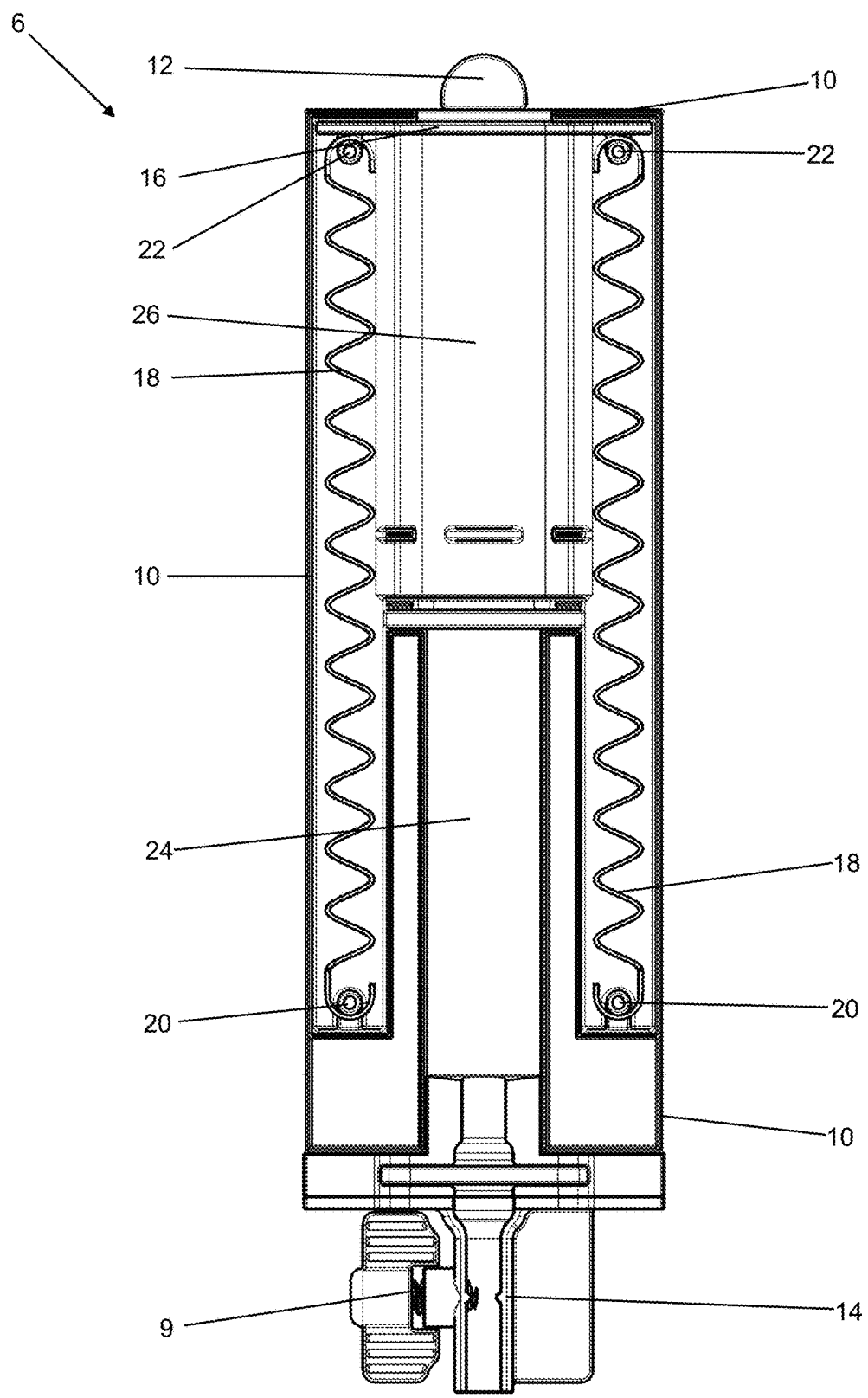
FIG. 7: is a schematic partial cross-sectional plan view of the conveying device according to FIG. 6 in the tensioned state.
Figure 8:
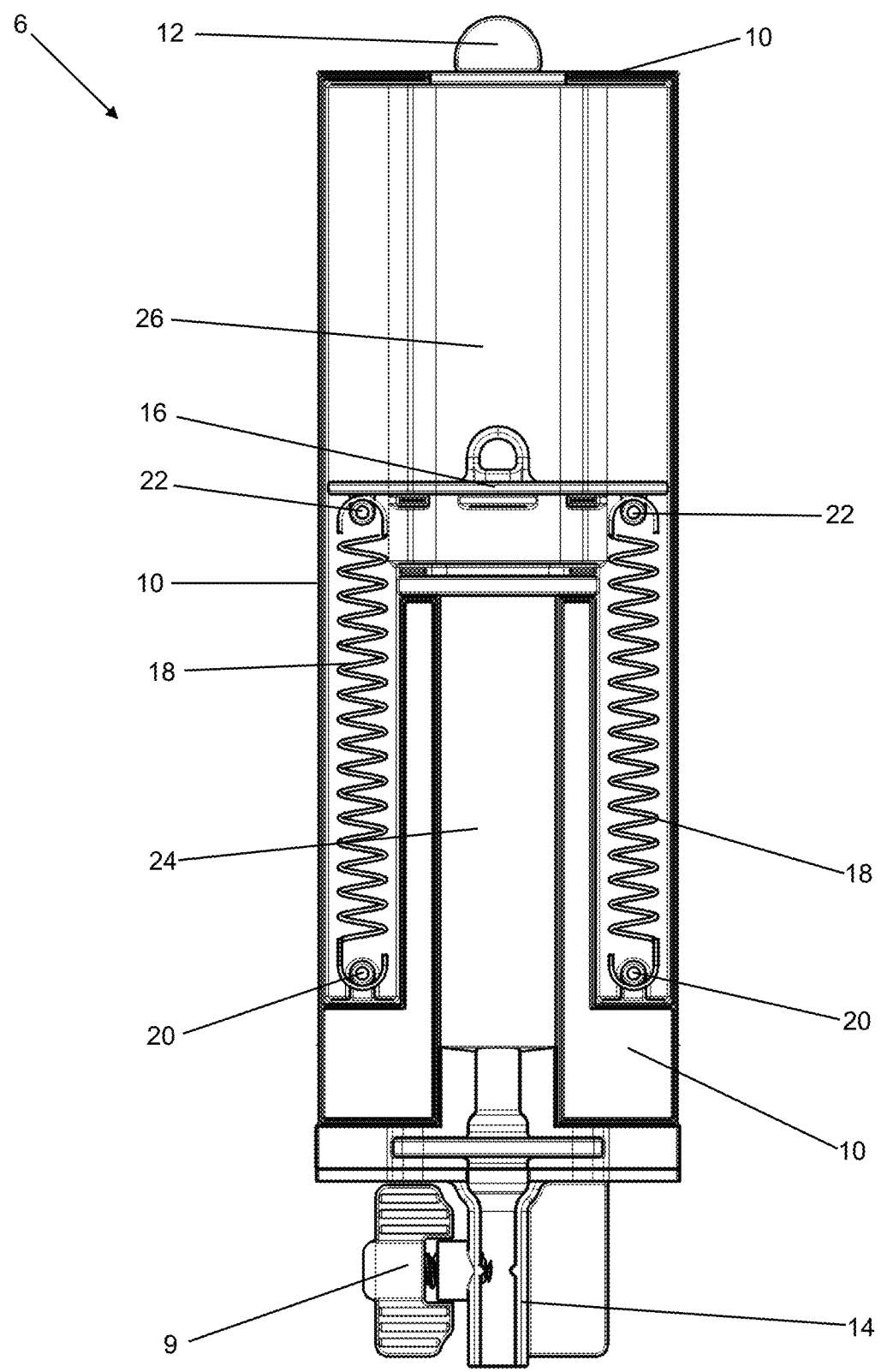
FIG. 8: is a schematic partial cross-sectional plan view of the conveying device according to FIG. 6 in the non-tensioned state.
Figure 9:
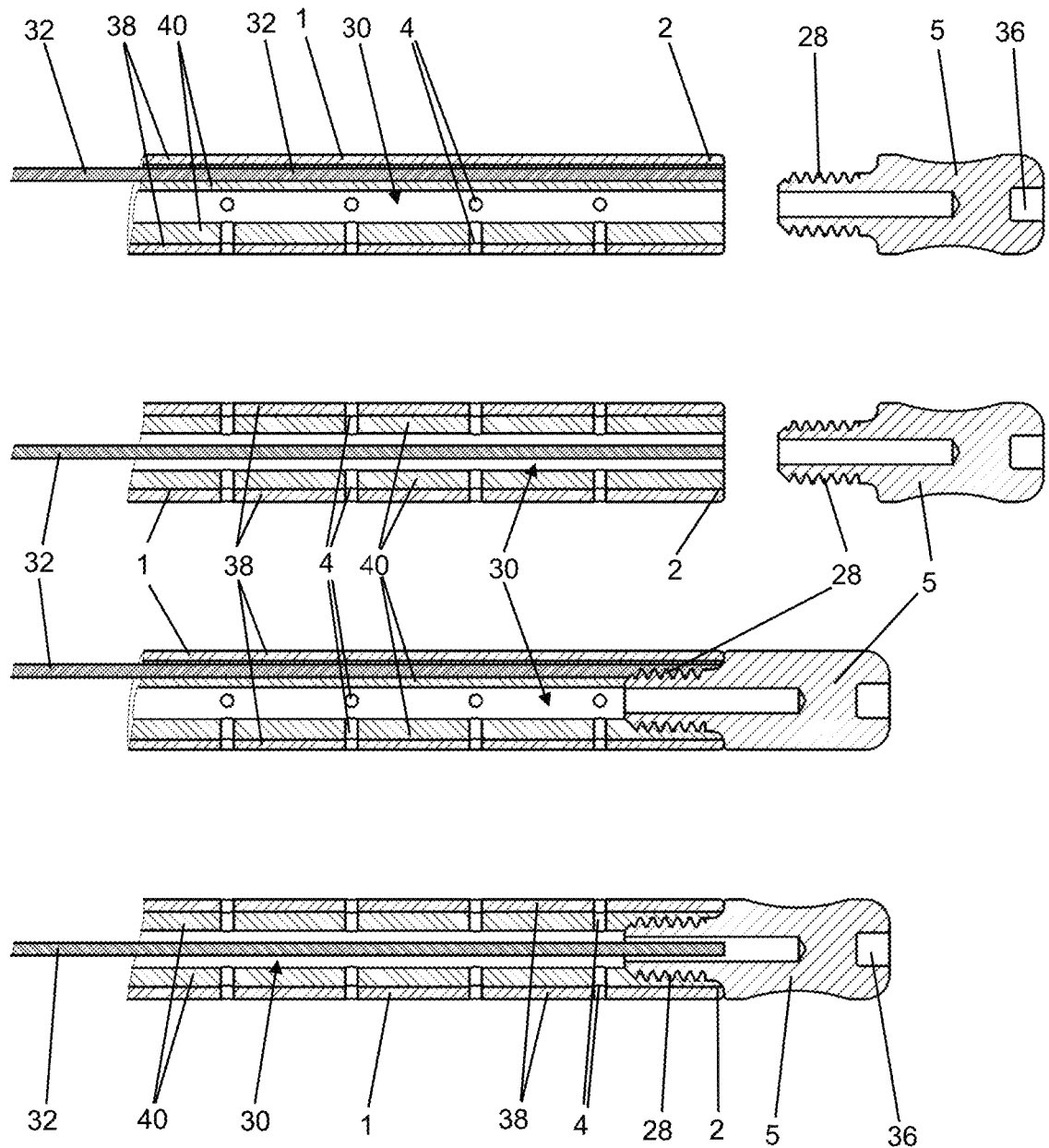
FIG. 9: illustrates four schematic cross-sectional views of distal tube portions of two devices according to the embodiment, with opened openings.
Figure 10:
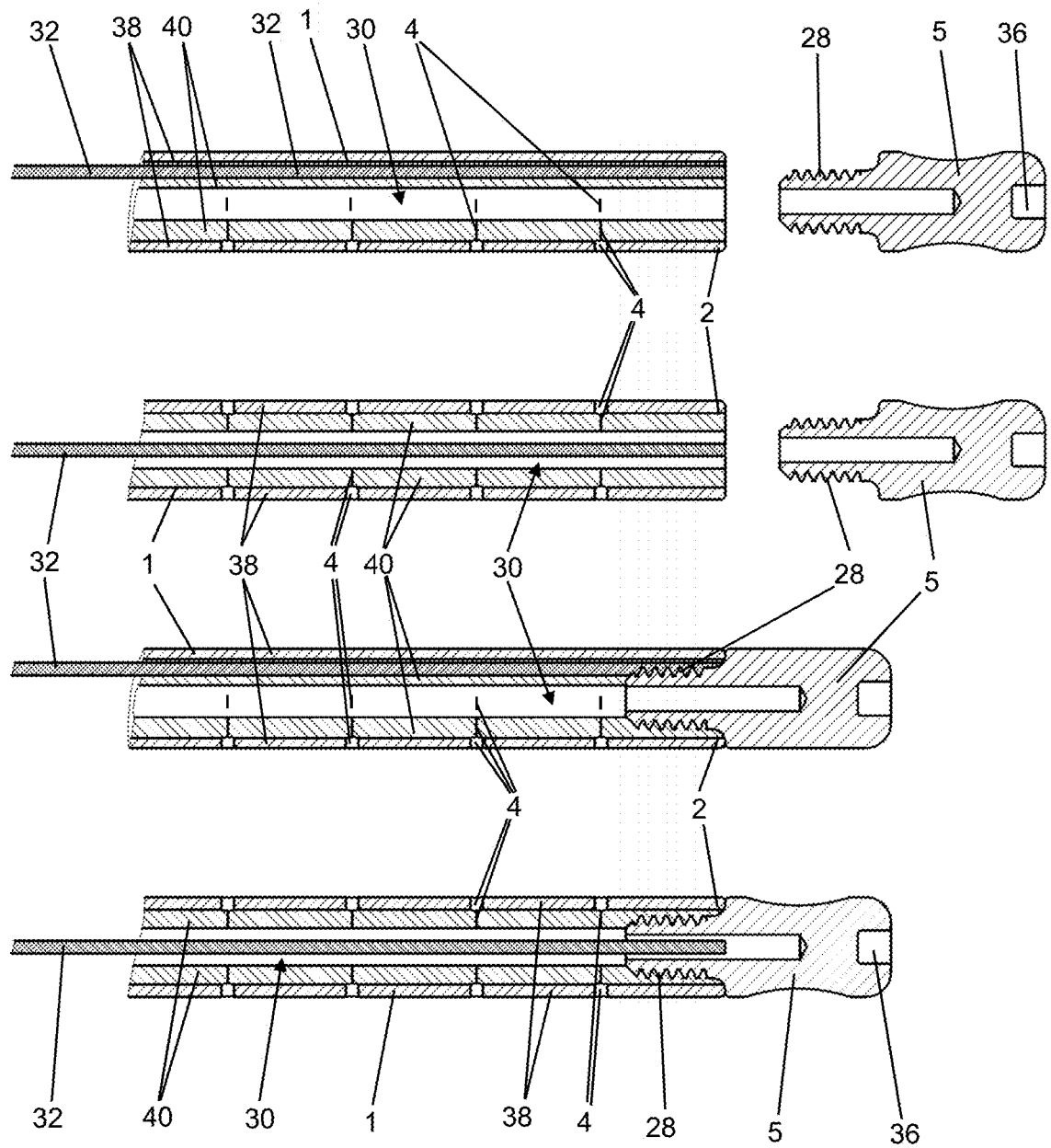
FIG. 10: illustrates four schematic cross-sectional views of the distal tube portions of the two devices according to FIG. 9, with closed openings.
Figure 11:
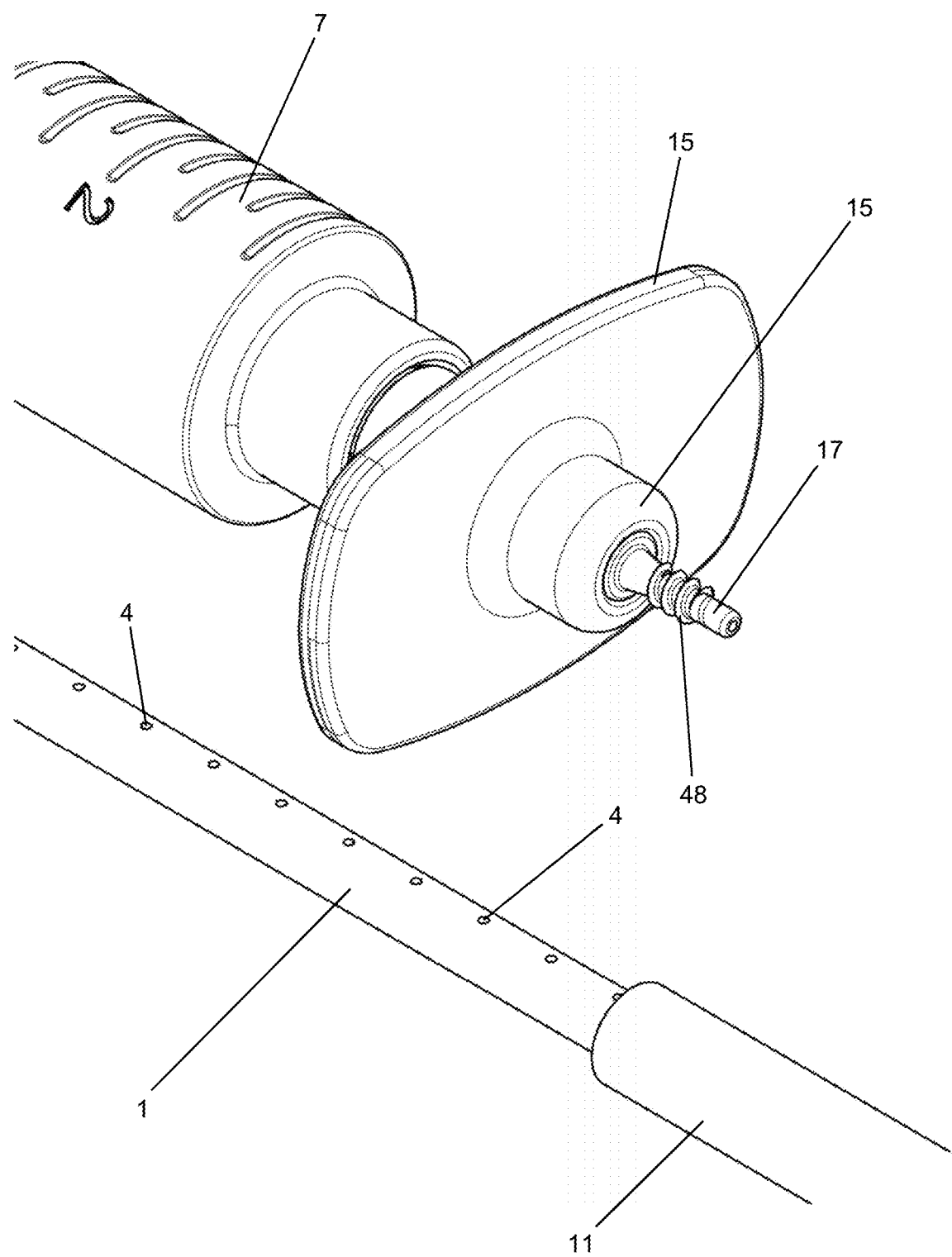
FIG. 11: is an enlarged detail from FIG. 2.
Figure 12:
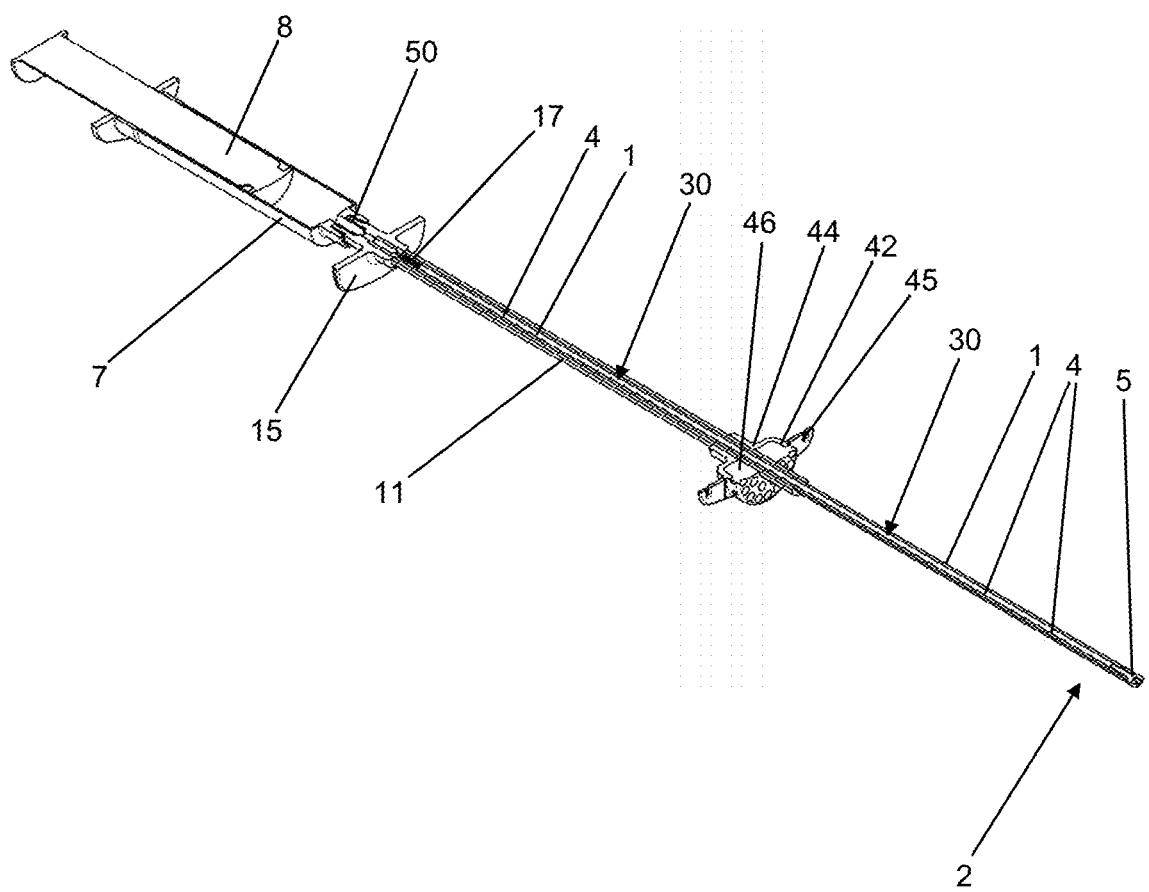
FIG. 12: is a schematic perspective cross-sectional view of the device according to FIG. 5, in which the shortened tube has been connected to the connector.
Figure 13:
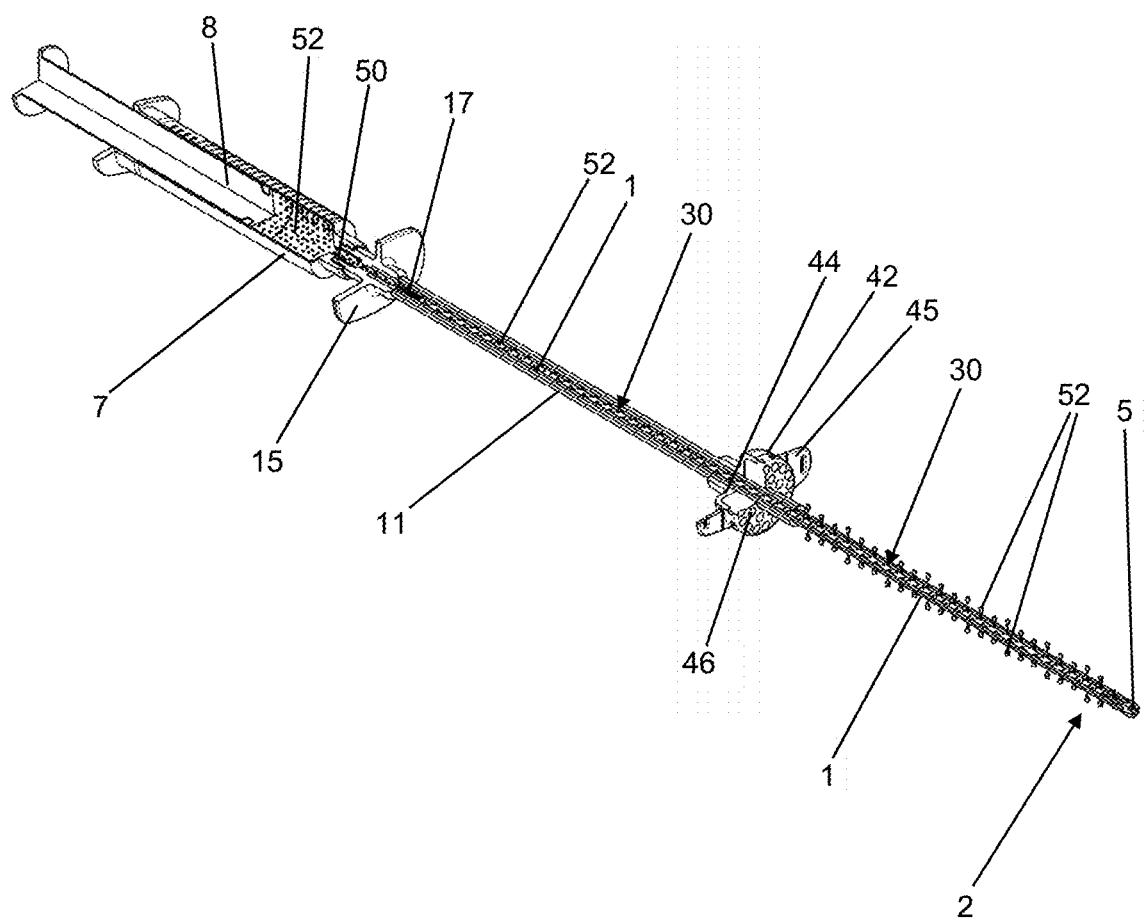
FIG. 13: is a schematic perspective partial cross-sectional view of the device according to FIGS. 1 to 5 and 11 and 12 while a medical fluid is being pushed out.
Figure 14:
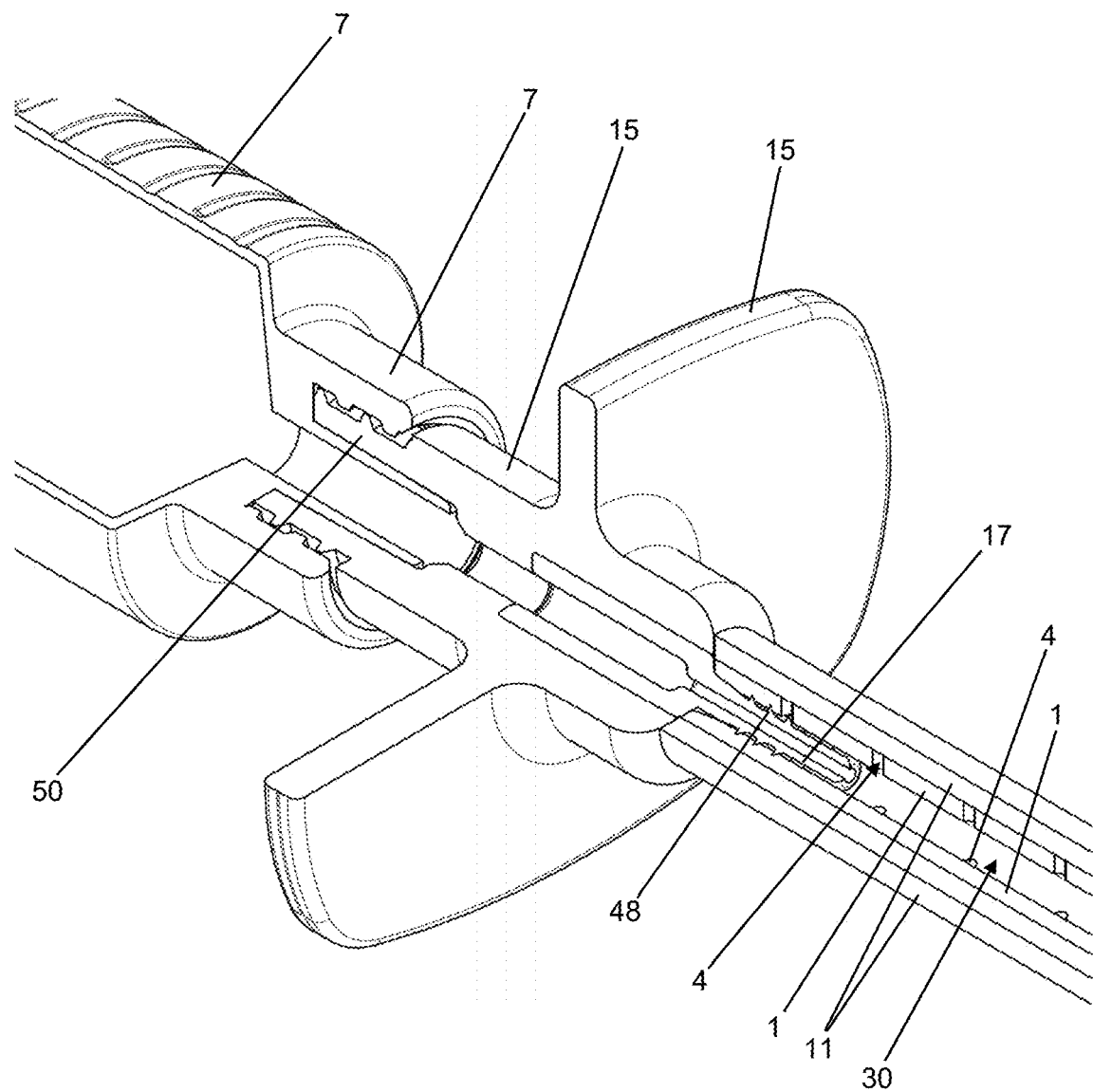
FIG. 14: is a schematic perspective cross-sectional view of the device according to FIG. 5 as an enlarged detail in the region of the connector.
Figure 15:
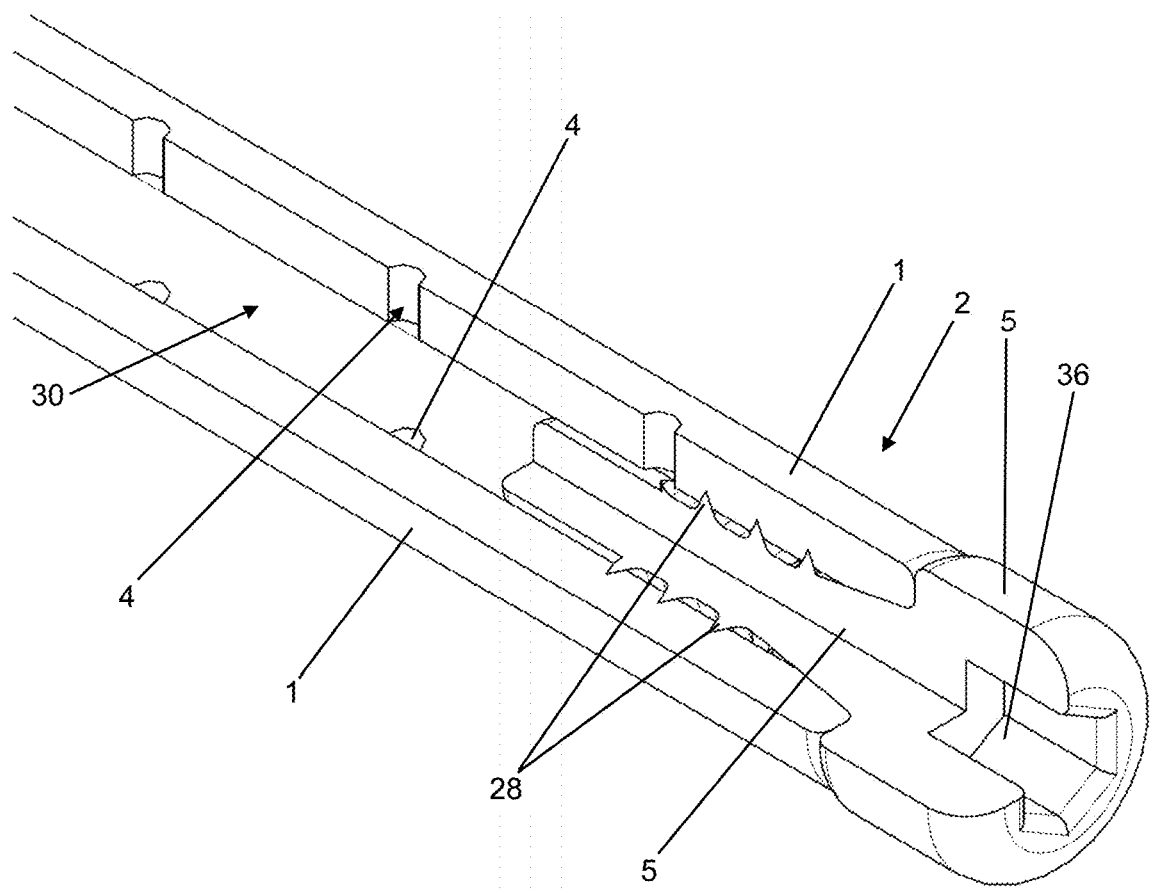
FIG. 15: is a schematic perspective cross-sectional view of the device according to FIGS. 1 to 5 and 11 to 14 as an enlarged detail in the region of the distal tube end of the tube.
Figure 16:
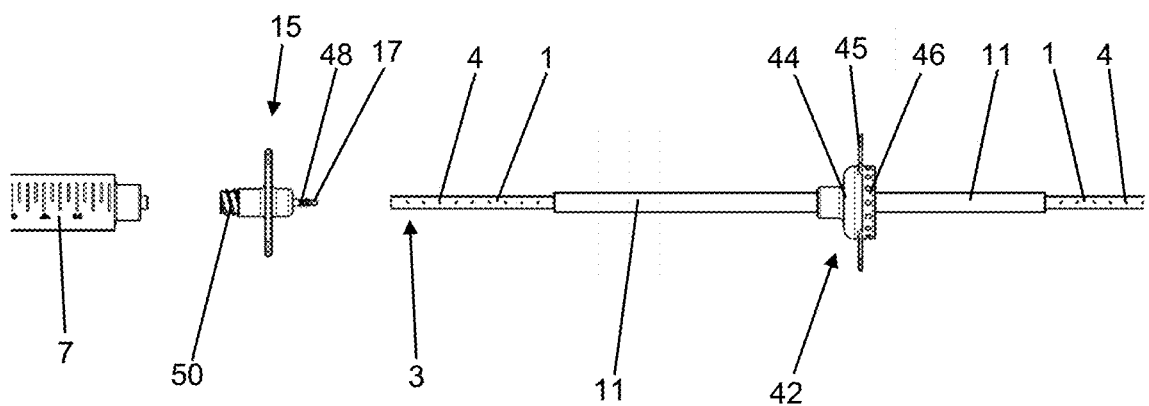
FIG. 16: is a schematic side view as an enlarged detail of a device according to the embodiment, in which the connector is disconnected from the container and the tube.
Figure 17:
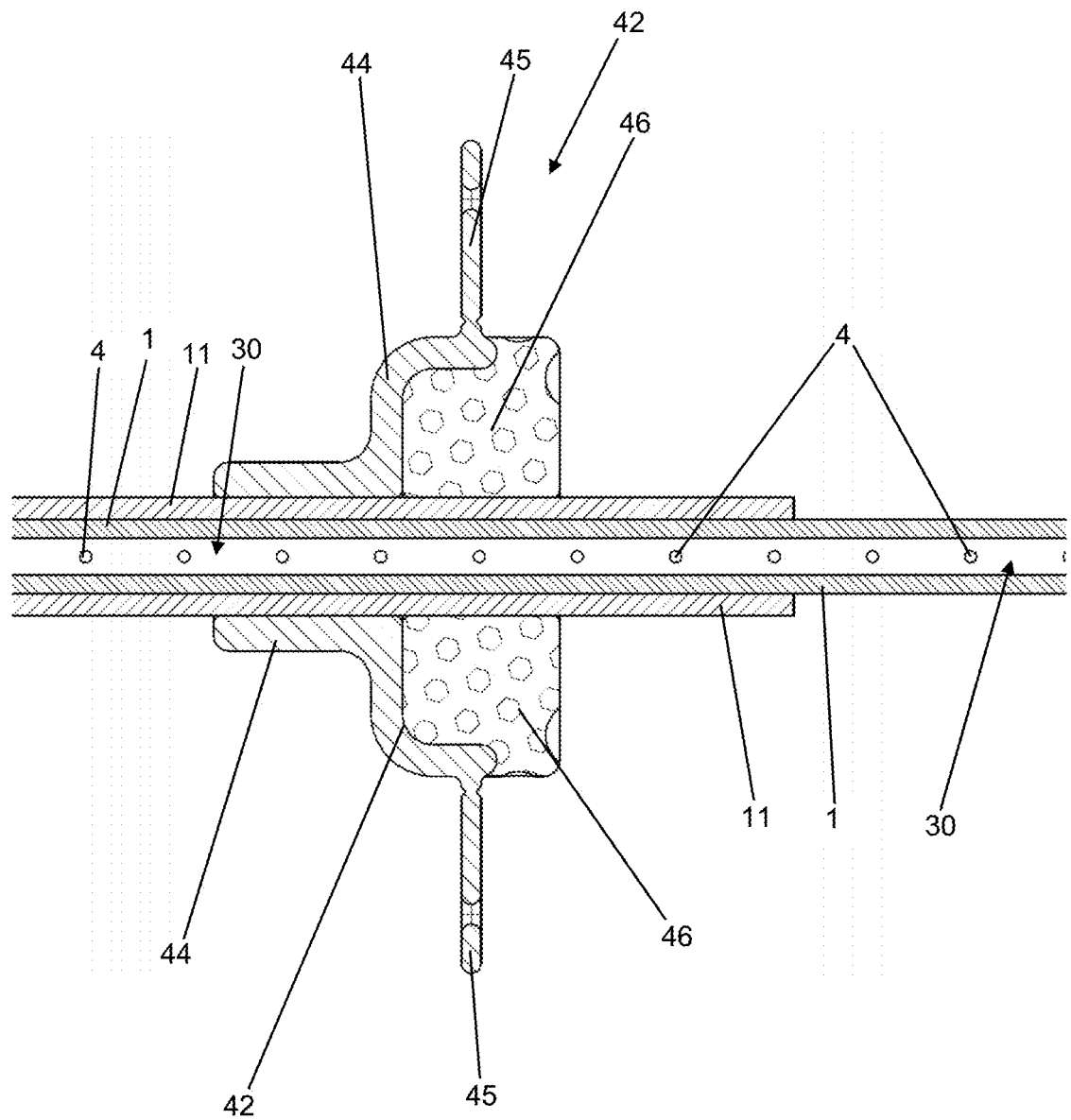
FIG. 17: is a schematic partial cross-sectional view in the region of a seal element of a device according to the embodiment as an enlarged detail.
Figure 18:
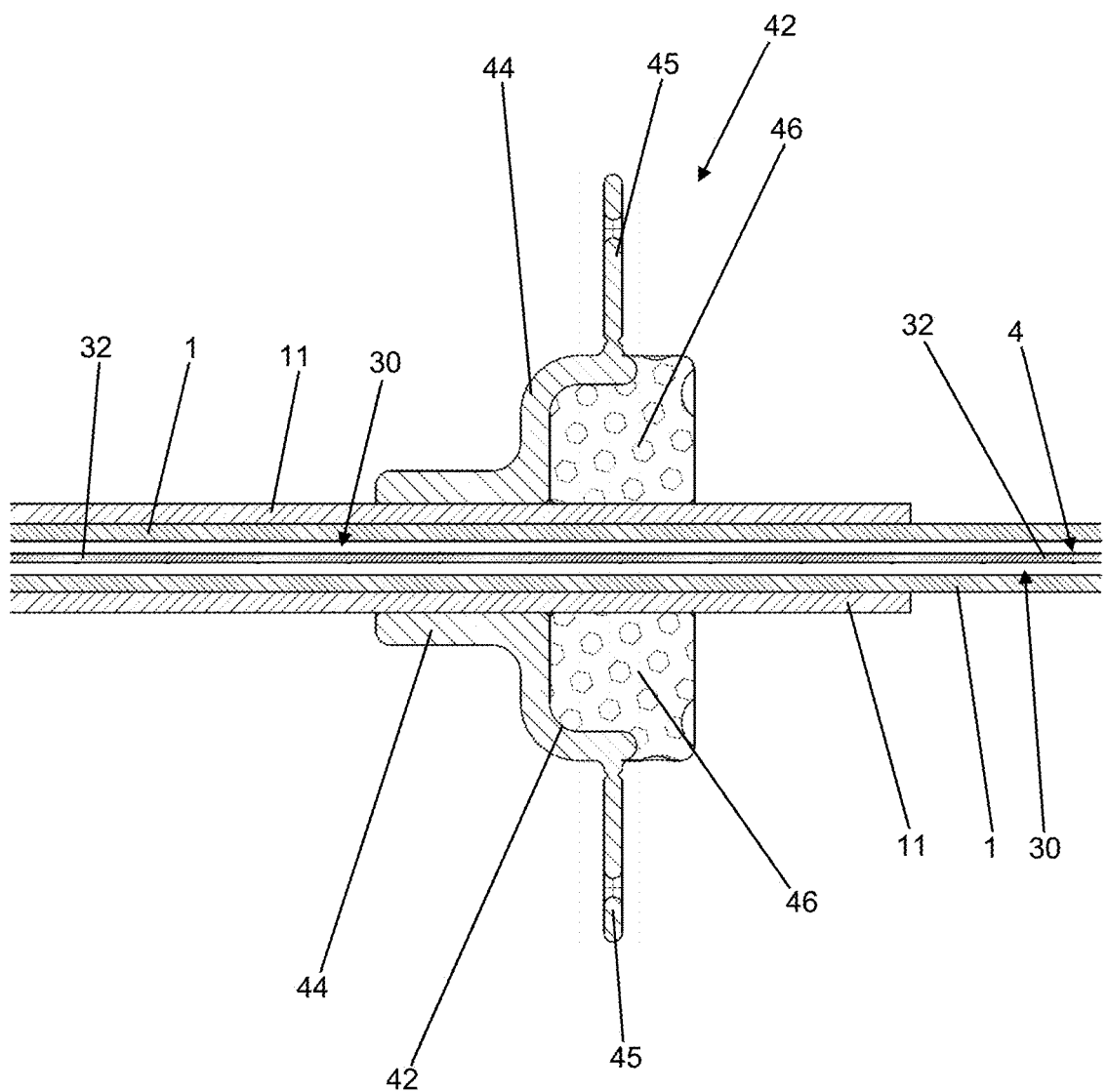
FIG. 18: is a schematic partial cross-sectional view in the region of a seal element of a further device according to the embodiment as an enlarged detail.

FIGS. 1 to 5 and 11 to 17 show a first example device according to the embodiment and parts thereof in various views. FIGS. 6 to 8 show a conveying device of a device according to the embodiment, for pushing out a medical fluid. FIGS. 9 and 10 show open and closed distal tube end portions as parts of two different example embodiments according to the embodiment. FIGS. 11 and 14 to 19 show enlarged details of devices according to the embodiment. FIGS. 12 and 13 are a cross-sectional view and a partial cross-sectional view of the first device according to the embodiment.

Figure 2:
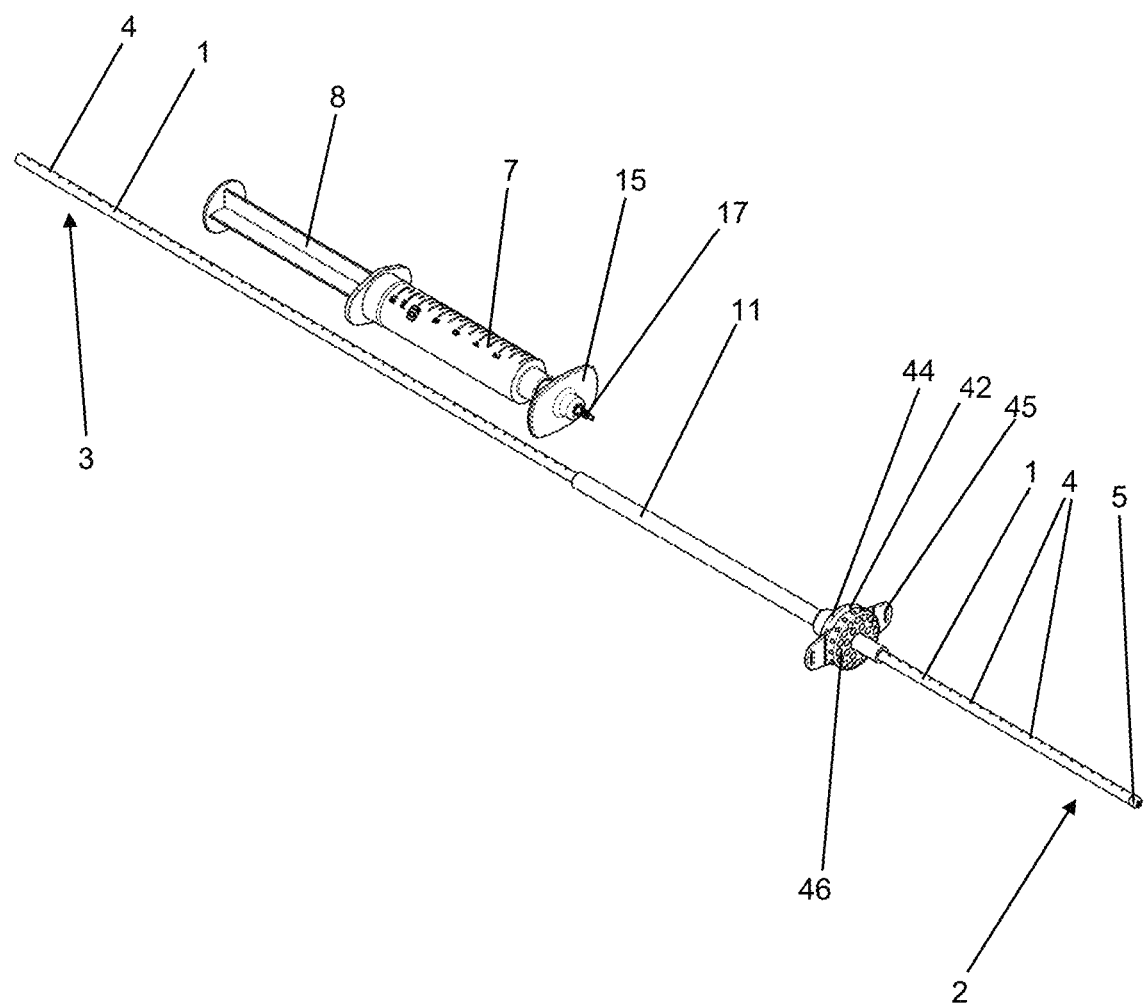
FIG. 2: is a schematic perspective view of the device according to FIG. 1, in which a tube of the device is not connected to a connector.
Figure 3:
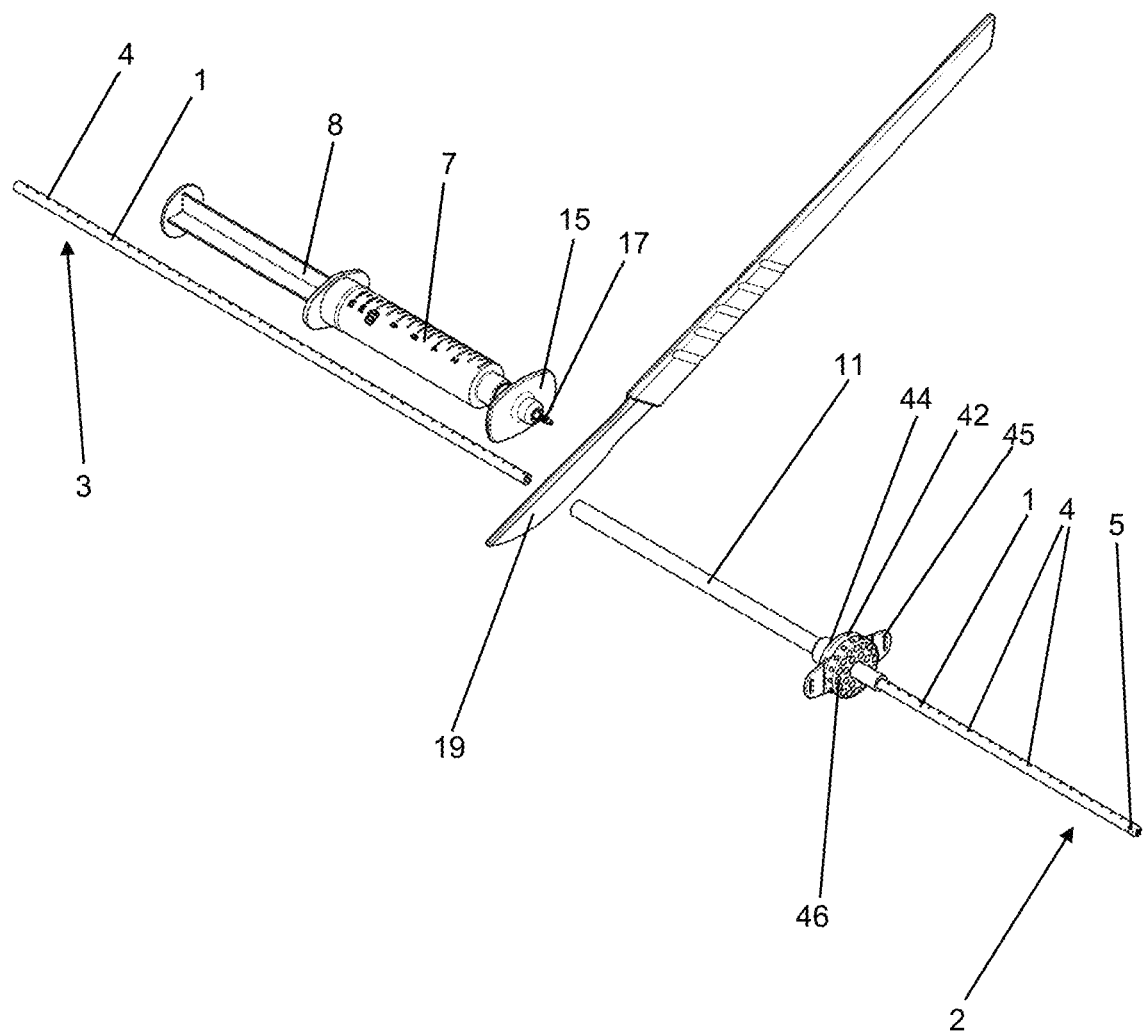
FIG. 3: is a schematic perspective view of the device according to FIG. 2, in which the tube has been shortened.
Figure 4:
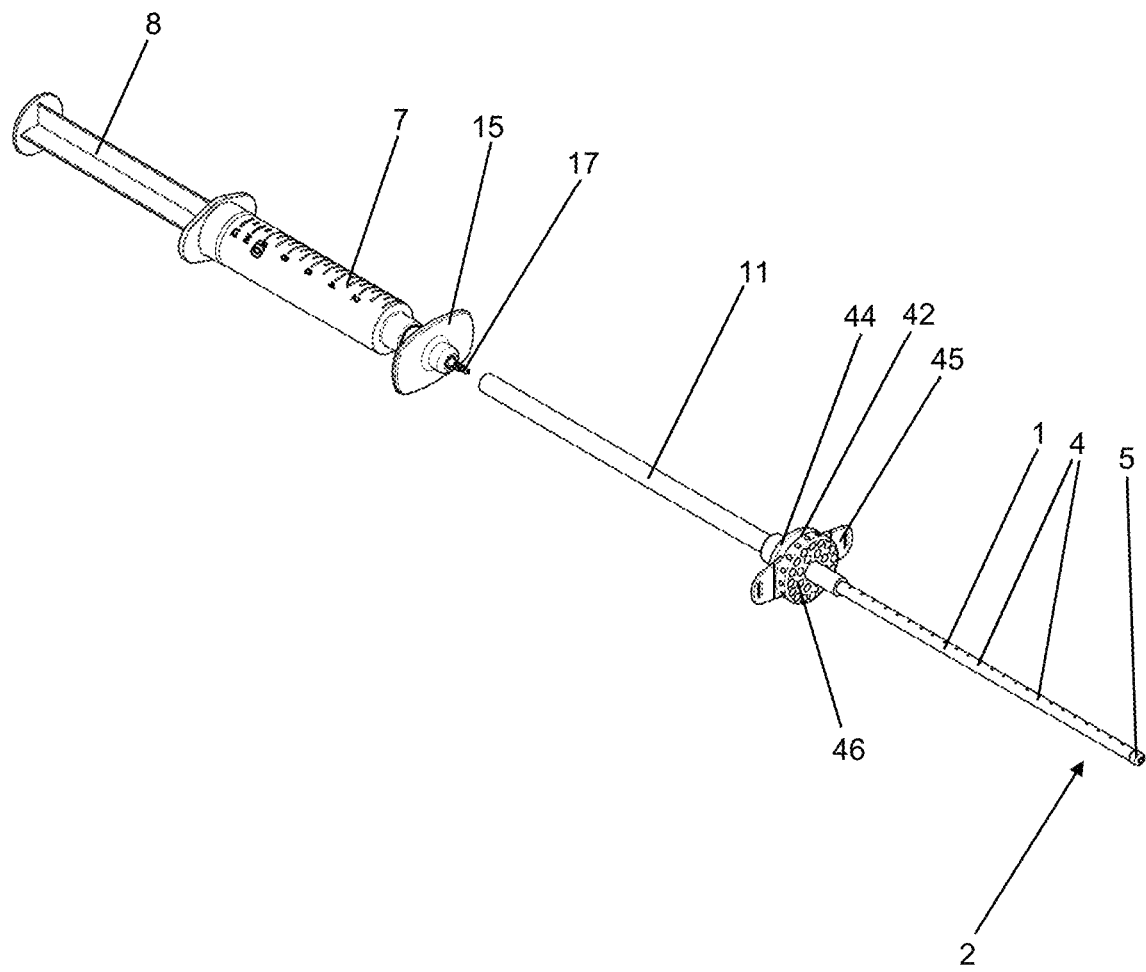
FIG. 4: is a schematic perspective view of the device according to FIG. 3, in which the shortened tube has not yet been connected to the connector.
Figure 5:
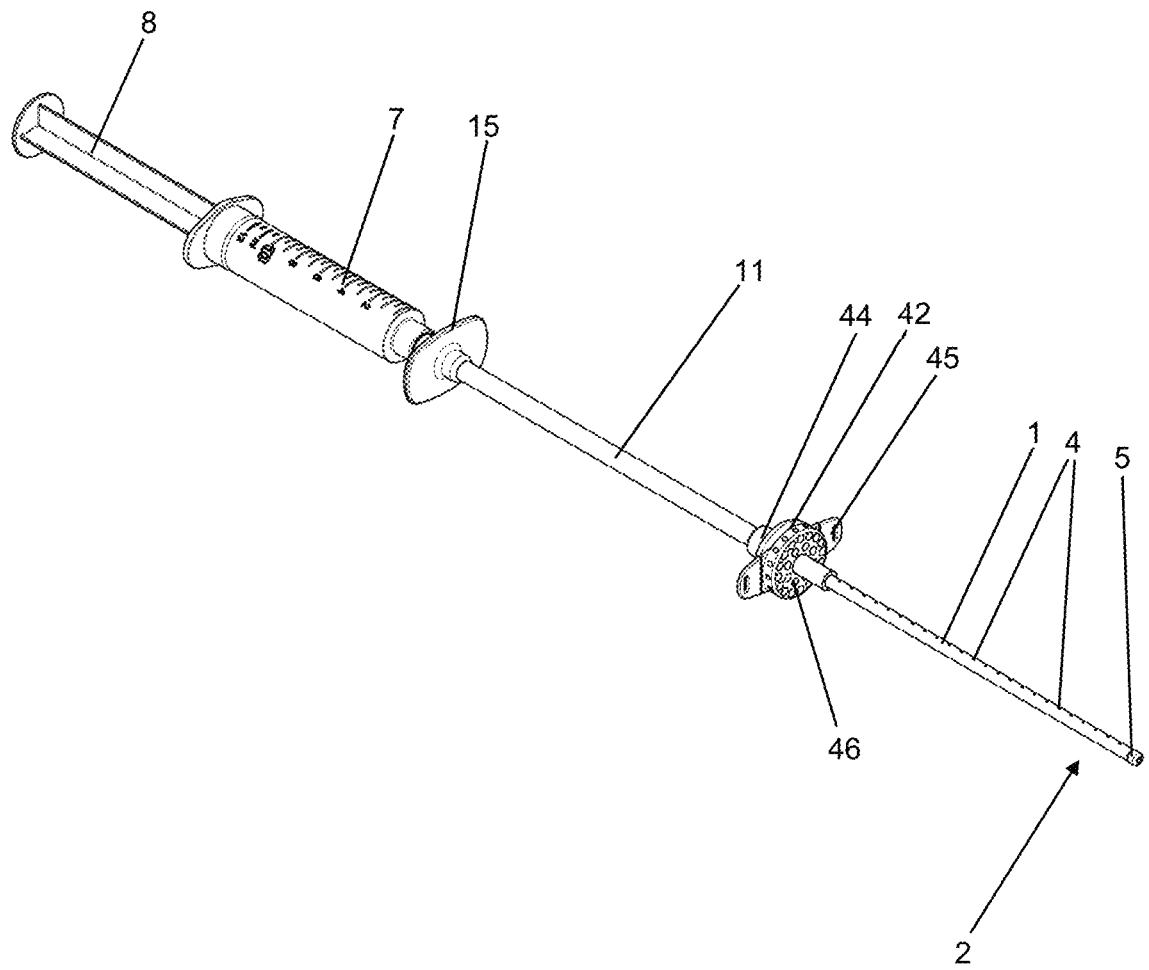
FIG. 5: is a schematic perspective view of the device according to FIG. 4, in which the shortened tube has been connected to the connector.

The first example device according to one embodiment, illustrated in FIGS. 1 to 5 and 11 to 17, has a tube 1 on the front distal side (at the bottom on the right in FIGS. 1, 4, 5, 12 and 13, and at the bottom in FIGS. 2 and 3). The tube 1 may include a distal tube end 2 and a proximal tube end 3 opposite the distal tube end 2 (see FIGS. 2 and 3). A plurality of openings 4 passing through the tube wall and extending as far as an inner line 30 (not visible in FIGS. 1 to 5 but visible in FIGS. 12 to 15) of the tube 1 may be made in the tube 1. The tube 1 may be plastically deformable such that the shape of the tube 1 can be adapted to the shape of a hollow space to be flushed.

On the tube 1, an outer sleeve 11 that is axially movable on the tube 1 may be arranged, in the form of a tube portion that is shorter than the tube 1 or in the form of a pipe that is shorter than the tube 1. The outer sleeve 11 may have an inner diameter that matches the outer diameter of the tube 1 such that the outer sleeve 11 covers and fluid-tightly closes those openings 4 in the tube wall above which the outer sleeve is arranged. This ensures that a medical fluid 52 (see FIG. 13) applied by a device of this kind only escapes from the device within the hollow space to be flushed.

The tube 1 may be fluid-tightly and pressure-tightly closed by a closure element 5 at the distal tube end 2 of the tube. The tube 1 includes an inner wall 40 and an outer wall 38 (not visible in FIGS. 1 to 5 and 11 to 17, but of a structure similar to that in FIGS. 9 and 10), the outer wall 38 surrounding, in one embodiment coaxially, the inner wall 40.

The openings 4 extend through the outer wall 38 and the inner wall 40. Inside the tube 1, the inner line 30 is in one embodiment delimited by the inner wall 40. The openings 4 can liquid-permeably connect the inner line 30 to the surroundings of the tube 1. The inner wall 40 may consist of an elastically deformable material such as a rubber-elastic polymer, in particular polyurethane. The outer wall 38 may consist of a non-rubber-elastic thermoplastic polymer, in particular polyamide. As a result, the inner wall 40 is elastically deformable while the outer wall 38 is largely dimensionally stable with respect to radial expansion of the tube 1. The material for the outer wall 38 may be selected such that deformation of the longitudinal axis of the tube 1 is possible, while radial expansion of the tube 1 owing to internal pressure in the inner line 30 is not possible, or a maximum of 5% relative axial expansion is possible.

The openings 4 may be pierced through the inner wall 40 of the tube 1 such that the material of the inner wall 40 is not punched out. In a manner similar to rubber-elastic membranes for containers for filling syringes, the openings 4 in the inner wall 40 can thus close (see FIG. 10). If pressure is exerted on a fluid in the inner line 30, the pressure opens the openings 4 in the inner walls 40 of the tube 1 (see FIG. 9), and the fluid can emerge from the openings 4, as is indicated in FIG. 13 by the emerging droplets of the medical fluid 52.

The openings 4 may be radially distributed and distributed along the entire length of the tube 1. The openings 4 in four axial directions indicated in the example embodiment are to be merely understood as an example. The tube 1 may also be adjusted to the size of the hollow space to be flushed, by the tube being cut shorter on a proximal side (see FIG. 3). A connector 15 allows the new cut proximal tube end to be fluid-tightly connected to a container 7 for holding the medical fluid 52. For this purpose, a connection 17 of the connector 15 may be inserted or screwed into the inner line 30. For this purpose, an outer thread 48 may be arranged on the connection 17 of the connector 15 (see FIGS. 11 and 16), the outer thread being screwable into the proximal tube end of the tube 1. On the proximal side of the connector 15 opposite the connection 17, a connecting piece 50 having an outer thread (see FIGS. 12, 13 and 16) or having a Luer lock connection may be arranged, the connecting piece allowing the connector 15 to be fluid-tightly connected to the container 7.

On the proximal side of the device, a conveying device 6 (see FIGS. 6 to 8) may be arranged. The container 7, in the form of a syringe having a piston 8 for pushing out the contents of the syringe, may be or have been inserted into the conveying device 6. The piston 8 may be arranged so as to be movable in the axial direction in the syringe and may be fluid-tightly sealed against the inner wall of the container 7. The conveying device 6 may include a housing 10 that is made of plastic and may entirely or partially externally close the interior of the conveying device 6. A securing bolt 12 may be inserted into an opening at the proximal end of the housing 10.

On the distal side of the conveying device 6, a holder 14 for fastening the connector 15 to the tube 1 may be arranged. For this purpose, the connector 15 may include a holder disc that can engage in the holder 14.

In the conveying device 6, a conveying panel 16 for pushing the piston 8 into the container 7 may be arranged. The securing bolt 12 allows the conveying panel 16 to be locked against the housing 10. For this purpose, a loop may protrude out of the housing 10 of the conveying device 6 on the proximal side of the conveying panel 16, and the conveying panel 16 may be locked against the housing 10 by inserting the securing bolt 12. The conveying panel 16 may be driven by two tensioned springs 18. The two springs 18 are an energy storage element that stores at least the energy required to push out a medical fluid 52 from the container 7 and through the tube 1 and through the openings 4 of the tube 1.

The springs 18 may be fastened, at the distal ends thereof, to the housing 10 by using pins 20. At the proximal ends thereof, the springs 18 may be fastened to the conveying panel 16 by using pins 22. The springs 18 can thus be tensioned between the pins 20 and the pins 22.

Within the housing 10, a receptacle 24 for the container 7 and a stroke chamber 26 for the piston 8 may be formed. The container 7 may be fixed in the conveying device 6 through the shape of the receptacle 24. In this way, the conveying panel 16 can be pulled from the proximal end to the distal end of the stroke chamber 26 by the springs 18 (see FIGS. 7 and 8). In the conveying device 6, and driven by the springs 18, the piston 8 can be pushed into the container 7 by the conveying panel 16 when the securing bolt 12 has been removed and the valve element 9 is open. As a result, a medical fluid 52 contained in the container 7 can be pushed out of the container 7 and through the tube 1 and the openings 4 in the tube 1. The pressure acting on the medical fluid 52 allows the openings 4 in the inner wall of the tube 1 to be opened.

The tubes 1 illustrated in FIGS. 9 and 10 can be readily used in the device illustrated in FIGS. 1 to 5 and 11 to 17, and FIGS. 9 and 10 are thus understood to depict details of the first example embodiment. The variants of the tubes 1 according to FIGS. 9, 10 and 18 differ in the arrangement of a metal wire 32 that may be arranged in the inner line 30 of the tube 1 or in the tube wall. The structure according to FIG. 18 corresponds to that according to FIG. 17, except for the metal wire 32, which is arranged in the inner line 30 of the tube 1 to allow the tube 1 to plastically deform. If the metal wire 32 is arranged in the inner line 30, the metal wire 32 may have a smaller diameter than the inner diameter of the inner line 30 so that the inner line 30 has a sufficient open cross section for guiding the medical fluid 52.

In all cases, the tube 1 may be closable, at the distal tube end 2 thereof, by a closure element 5. The closure element 5 may include a protruding cylindrical projection having an outer thread 28. The outer thread 28 allows the closure element 5 to be screwed into the open inner line 30 of the tube 1. The closure element 5 in one embodiment consists of metal. The outer thread 28 can cut a matching inner thread into the inner wall of the tube 1. As a result, the tube 1 can be liquid-tightly and pressure-tightly closed at the distal tube end 2 thereof. In the distal head of the closure element 5, an inner hexagon 36 may be arranged, or another screw head may be arranged, in order to be able to more conveniently screw the closure element 5 into the tube 1.

In a manner similar to the first example embodiment according to FIGS. 1 to 5 and 11 to 17, the tube 1 includes an outer wall 38 and an inner wall 40 (see FIGS. 9 and 10). The outer wall 38 in one embodiment completely surrounds the inner wall 40. The materials for forming the outer wall 38 and the inner wall 40 may be selected in a similar manner to the first example embodiment such that the outer wall 38 is dimensionally stable and the inner wall 40 is rubber-elastic. A plurality of openings 4 extend through the outer wall 38 and the inner wall 40 as far as the inner line 30 of the tube 1.

If pressure of a medical fluid is not acting in the inner line 30 of the tube 1, tension in the material of the inner wall 40 can be relieved. The openings 4 are thus fluid-tightly closed in the inner wall 40 (see FIG. 10). The openings 4 are visible as slots in the inner wall 40 in FIG. 10. Pressure on the medical fluid allows the openings 4 in the inner wall 40 to be opened. In the process, the tube 1 is not radially expanded since the outer wall 38 can absorb the forces. The medical fluid can emerge via the opened openings 4.

In both embodiments, the metal wire 32 allows the tube 1 to be plastically deformed and maintain the shape thereof.

In the first example embodiment, a seal element 42 may be pushed onto the tube 1. The seal element 42 may in one embodiment be axially (in relation to the cylindrical tube axis) movable on the tube 1, in particular together with the outer sleeve 11 (see also FIG. 17). The seal element 42 may be rigidly connected to the outer sleeve 11. According to one embodiment, the seal element 42 is arranged in the region of the distal end of the outer sleeve 11. The user can thus see where the distal portion of the tube 1 to be implanted ends or where the adjoining proximal portion of the tube 1 not to be implanted begins. In addition, the outer sleeve 11 can thus be conveniently moved on the tube 1, together with the seal element 42.

The seal element 42 may be in the form of a sleeve and include an outer sleeve shape 44 having two holder wings 45, and a distal sponge sleeve 46. The sponge sleeve 46 may be soaked in an antibiotic and/or disinfectant solution. The seal element 42 may be pushed onto an entry opening in a body and thus prevent germs from entering the entry opening. The holder wings 45 allow the seal element 42 to be fastened to the skin of a patient or to an implant.

The device according to the embodiment is used in such a way that the medical personnel determines the length of the cavity to be treated or the medical implant. On the tube 1, the outer sleeve 11, in the form of the outer tube, is then pushed towards the distal tube end 2 until the distal end of the outer sleeve 11 reaches the edge of the cavity to be treated or the medical implant (see FIG. 2). The tube 1 protruding from the proximal end of the outer sleeve 11 is then cut directly adjacent to the proximal end of the outer sleeve 11 (see FIG. 3). The new proximal tube end of the tube 1 is closed by screwing or pushing the connector 15 in (see the transition from FIG. 4 to FIG. 5), the connector 15 pressing the outside of the tube 1 against the inside of the outer sleeve 11 (see FIGS. 13 and 14). The connector 15 is liquid-permeably connected or connectable to the container 7 containing the fluid reservoir (see FIG. 13). Subsequently, the piston 8 allows the medical fluid 52 to be pushed out of the container 7 through the connector 15 and through the inner line 30 of the tube 1 out of the exposed openings 4 on the distal side of the tube 1 (see FIG. 13). In the process, the outer sleeve 11 prevents the medical fluid 52 from being able to emerge from the openings 4 on the proximal side of the tube 1 that are arranged outside the cavity to be treated or the medical implant.

Depending on the application, a disinfecting liquid or an aqueous solution including at least one antibiotic and/or at least one antimycotic agent, for example, may be used as the medical fluid 52 to be applied. Furthermore, the medical fluid 52 may also contain at least one cytostatic agent and/or at least one chemotherapeutic agent.

For a medical application of the devices according to one embodiment, the tube 1 and in one embodiment also the closure elements 5 may be made up of biocompatible materials containing X-ray-opaque substances such that the position of the tube 1 and optionally the closure element 5 can be determined by X-ray imaging methods.

The features of embodiments disclosed in the preceding description and in the claims, drawings and example embodiments may be essential, both individually and in any combination, for implementing the various embodiments thereof.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

The invention claimed is:

1. A device for locally applying a medical fluid, comprising
- a tube, the tube being flexibly deformable and comprising a tube wall;
- wherein the tube comprises a plurality of openings in the tube wall, the plurality of openings connecting an inner line of the tube to the surroundings of the tube, and the tube being closed at a distal tube end of the tube;
- wherein a proximal tube end of the tube is liquid-permeably connected or connectable to a container for the medical fluid such that the medical fluid from the container can be pushed through the proximal tube end of the tube into the inner line of the tube and can be pushed out through the plurality of openings into the surroundings of the tube; and
- wherein the device comprises an outer sleeve for fluid-tightly closing a subset of the plurality of openings, the outer sleeve being axially movably arranged around the tube, and the outer sleeve being shorter than the tube such that the distal openings that are not part of the closed subset of the plurality of openings are exposed; and
- wherein the tube wall comprises an outer wall that is made of a first material and is arranged radially externally, and the tube wall comprises an inner wall that is made of a second material, is arranged radially internally and delimits the inner line of the tube, wherein the outer wall and the inner wall are rigidly interconnected and such that the first and second materials allow the outer and inner walls to respond differently to physical or chemical parameters, wherein the plurality of openings in the inner wall or the outer wall are slot-shaped and have an open cross section which, when hydrostatic pressure of 500 kPa is applied by the medical fluid, is larger by a factor of two or more than when pressure is not applied.

2. A device for locally applying a medical fluid, comprising
- a tube, the tube being flexibly deformable and comprising a tube wall;
- wherein the tube comprises a plurality of openings in the tube wall, the plurality of openings connecting an inner line of the tube to the surroundings of the tube, and the tube being closed at a distal tube end of the tube;
- wherein a proximal tube end of the tube is liquid-permeably connected or connectable to a container for the medical fluid such that the medical fluid from the container can be pushed through the proximal tube end of the tube into the inner line of the tube and can be pushed out through the plurality of openings into the surroundings of the tube, and
- wherein the device comprises an outer sleeve for fluid-tightly closing a subset of the plurality of openings, the outer sleeve being axially movable arranged around the tube, and the outer sleeve being shorter than the tube such that the distal openings that are not part of the closed subset of the plurality of openings are exposed, and wherein the tube wall comprises an outer wall that is made of a first material and is arranged radially externally, and the tube wall comprises an inner wall that is made of a second material, is arranged radially internally and delimits the inner line of the tube, wherein the outer wall and the inner wall are rigidly interconnected and such that the first and second materials allow the outer and inner walls to respond differently to physical or chemical parameters, and wherein the plurality of openings in the outer wall of the tube wall are open irrespective of the pressure of the medical fluid, while the plurality of openings in the inner wall of the tube wall are closed by the medical fluid without pressure being applied and are liquid-permeably openable by using pressure on the medical fluid.

3. The device according to claim 1, wherein the outer wall of the tube wall absorbs pressure of the medical fluid in the inner line, transmitted via the inner wall of the tube wall, without radially expanding by more than 1%.

4. The device according to claim 1, wherein the first material has a larger Shore A hardness than the second material, first material having a Shore A hardness of more than 60, and the second material having a Shore A hardness of less than 60.

5. The device according to claim 1, wherein the plurality of openings in the tube in the outer wall have a diameter of at most 100 μm.

6. The device according to claim 1, wherein the tube is formed of a coaxial coextrudate, the inner wall consisting of a rubber-elastic polymer, in particular polyurethane or a weakly crosslinked polymer, and the outer wall consisting of a non-rubber-elastic thermoplastic polymer or of a strongly crosslinked polymer, in particular polyamide.

7. The device according to claim 1, wherein the device comprises a closure element, by using which the tube is fluid-tightly closed at the distal tube end of the tube.

8. The device according to claim 7, wherein the inner line of the tube starts at a proximal opening in the proximal tube end of the tube and ends at a distal opening in the distal tube end of the tube, the distal opening of the tube being closed by the closure element.

9. The device according to claim 1, wherein the device comprises the container for the medical fluid, the container comprising a hollow cylinder having a piston that is axially movable in the hollow cylinder and closes a first end of the hollow cylinder, the hollow cylinder comprising an output opening at an end opposite the first end, the output opening being connected or connectable to the proximal tube end of the tube, being connected or being connectable to the proximal tube end of the tube via a manually operable valve element for regulating the flow rate of the medical fluid, wherein a medical fluid, in particular a pharmaceutical fluid, is contained in the container.

10. The device according to claim 1, wherein the device comprises a conveying device, by using which the medical fluid is pushable out of the connected or connectable container into the tube, through the inner line of the tube and through the plurality of openings into the surroundings of the tube.

11. The device according to claim 10, wherein the conveying device comprises an energy storage element, in particular at least one tensioned spring, the conveying device being drivable with energy from the energy storage element, the energy storage element allowing a piston to be driven in a hollow cylinder as the container, towards an opposite output opening.

12. The device according to claim 1, wherein the device comprises a connector for connecting the tube to the container for the medical fluid, the connector comprising a conical or cylindrical projection that is inserted or screwed into the tube such that the tube is tensioned by the conical or cylindrical projection in the region of the proximal tube end of the tube such that the tube is fluid-tightly connected to the container at the proximal tube end of the tube and rigidly connected to the outer sleeve.

13. The device according to claim 12, wherein the conical or cylindrical projection comprises ribs on the outside of the conical or cylindrical projection, or the conical or cylindrical projection comprises an outer thread, the outer thread or the conical or cylindrical projection having a larger outer diameter than the inner diameter of the tube.

14. The device according to claim 1, wherein an X-ray-opaque material is contained in the tube at least at the distal tube end of the tube and/or in the closure element, an X-ray-opaque material being contained in a distal portion of the tube and, if present, in the closure element, being contained over the entire length of the tube and, if present, in the closure element.

15. The device according to claim 1, wherein at least one metal wire, at least one metal coil and/or at least one metal mesh is or are arranged in the inner line of the tube and/or in the tube wall of the tube, the at least one metal wire, the at least one metal coil and/or the at least one metal mesh being arranged along the entire length of the tube.

16. The device according to claim 1, wherein the total of the open cross-sectional areas of all of the plurality of openings is at most as large as the open cross section of the inner line.

17. The device according to claim 1, wherein with an internal pressure of 500 kPa, the tube expands radially by at most 5%, in relation to normal pressure.

18. A method for adjusting the tube length of a medical device for locally applying a medical fluid, the device comprising a tube having a tube wall, the tube comprising a plurality of openings in the tube wall, the plurality of openings connecting an inner line of the tube to the surroundings of the tube, and the device comprising an outer sleeve for fluid-tightly closing a proximal subset of the plurality of openings, the outer sleeve being axially movably arranged around the tube, and the outer sleeve being shorter than the tube such that the openings that are not part of the proximal subset of the plurality of openings are exposed, the method comprising:

A) Moving the outer sleeve on the tube until a desired distal length of the tube is exposed;
B) Cutting the proximal portion of the tube protruding beyond the outer sleeve;
C) Fixing the outer sleeve in relation to the tube; and
D) Connecting the new proximal tube end of the tube to a container for the medical fluid or to a connection for a container for the medical fluid such that the container is liquid-permeably connectable to the inner line of the tube.

19. The method according to claim 18, wherein in the method, no medical treatment of a human or animal body takes place, and/or the medical fluid is not administered to a human or animal body as part of the method.

20. The method applying a medical fluid according to claim 18, wherein the tube wall of the tube of the device comprises an outer wall that is made of a first material and is arranged radially externally, and the tube wall comprises an inner wall that is made of a second material, is arranged radially internally and delimits the inner line of the tube, the method further comprising:

Step E) Introducing a medical fluid into the tube;
Step F) Exerting pressure on the medical fluid in the tube;
Step G) Opening the plurality of openings in the inner wall or in the outer wall of the tube by using the pressure of the medical fluid acting on the plurality of openings; and
Step H) Driving out medical fluid through the opened plurality of openings.

21. The method according to claim 20, wherein a subsequent step I) Reducing the pressure on the medical fluid in the tube after step H) and thereby closing the plurality of openings in the inner wall of the tube or decreasing the open cross section of the plurality of openings in the inner wall of the tube.

22. The method according to claim 18, wherein the method is carried out using the device according to claim 1 or the method is carried out using a device for locally applying a medical fluid, the device comprising a tube, the tube being flexibly deformable and comprising a tube wall;
wherein the tube comprises a plurality of openings in the tube wall, the plurality of openings connecting an inner line of the tube to the surroundings of the tube, and the tube being closed at a distal tube end of the tube;
wherein a proximal tube end of the tube is liquid-permeably connected or connectable to a container for the medical fluid such that the medical fluid from the container can be pushed through the proximal tube end of the tube into the inner line of the tube and can be pushed out through the plurality of openings into the surroundings of the tube; and
wherein the device comprises an outer sleeve for fluid-tightly closing a subset of the plurality of openings, the outer sleeve being axially movably arranged around the tube, and the outer sleeve being shorter than the tube such that the distal openings that are not part of the closed subset of the plurality of openings are exposed.

* * * * *